US009381417B2

(12) United States Patent
Inoue

(10) Patent No.: US 9,381,417 B2
(45) Date of Patent: Jul. 5, 2016

(54) BICYCLE FITTING SYSTEM

(71) Applicant: Shimano Inc., Sakai, Osaka (JP)

(72) Inventor: Akira Inoue, Osaka (JP)

(73) Assignee: Shimano Inc., Osaka (JP)

( * ) Notice: Subject to any disclaimer, the term of this patent is extended or adjusted under 35 U.S.C. 154(b) by 195 days.

(21) Appl. No.: 13/968,435

(22) Filed: Aug. 16, 2013

(65) Prior Publication Data

US 2015/0051718 A1     Feb. 19, 2015

(51) Int. Cl.
*A63B 69/16* (2006.01)
*A63B 71/06* (2006.01)
*A61B 5/11* (2006.01)

(52) U.S. Cl.
CPC ............... *A63B 69/16* (2013.01); *A61B 5/1127* (2013.01); *A63B 71/06* (2013.01)

(58) Field of Classification Search
CPC ....................................................... G06F 19/00
USPC ............................................................ 700/91
See application file for complete search history.

(56) References Cited

U.S. PATENT DOCUMENTS

| | | |
|---|---|---|
| 5,077,619 A | 12/1991 | Toms |
| 5,198,877 A | 3/1993 | Schulz |
| 5,323,286 A | 6/1994 | Faul |
| 5,617,857 A | 4/1997 | Chader et al. |
| 5,622,170 A | 4/1997 | Schulz |
| 5,907,393 A | 5/1999 | Kawano et al. |
| 5,907,395 A | 5/1999 | Schulz et al. |
| 5,920,395 A | 7/1999 | Schulz |
| 5,987,349 A | 11/1999 | Schulz |
| 6,094,007 A | 7/2000 | Faul et al. |
| 6,141,104 A | 10/2000 | Schulz et al. |
| 6,442,416 B1 | 8/2002 | Schultz |
| 6,497,134 B1 | 12/2002 | Faul et al. |
| 6,608,688 B1 | 8/2003 | Faul et al. |
| 6,611,141 B1 | 8/2003 | Schulz et al. |
| RE39,102 E | 5/2006 | Schulz et al. |
| 7,256,899 B1 | 8/2007 | Faul et al. |
| 7,336,375 B1 | 2/2008 | Faul et al. |
| 7,742,804 B2 | 6/2010 | Faul |
| 8,224,423 B2 | 7/2012 | Faul |
| 8,294,082 B2 | 10/2012 | Melkis et al. |
| 2007/0142177 A1 | 6/2007 | Simms et al. |
| 2010/0076721 A1 | 3/2010 | Simms et al. |
| 2010/0306160 A1 | 12/2010 | Simms et al. |
| 2012/0086953 A1 | 4/2012 | Faul et al. |
| 2012/0262695 A1 | 10/2012 | Faul et al. |
| 2012/0323351 A1* | 12/2012 | Chen et al. ..................... 700/97 |
| 2013/0027716 A1 | 1/2013 | Melkis et al. |
| 2013/0065733 A1* | 3/2013 | Kautz et al. ..................... 482/57 |

OTHER PUBLICATIONS

"Watch a video on what a professional bike fitting is and how to find the best products for you!" published by FitWerx to YouTube on or before Jul. 1, 2009, printed from URL <https://www.youtube.com/watch?v=FsJYRaq-3sk>, 1 page.*

(Continued)

*Primary Examiner* — Jason Skaarup
(74) *Attorney, Agent, or Firm* — Global IP Counselors

(57) ABSTRACT

A bicycle fitting system includes a controller programmed to determine whether a current rider position of a rider is appropriate based on a flexibility level of a rider body of the rider.

15 Claims, 13 Drawing Sheets

(56) References Cited

OTHER PUBLICATIONS

"Competitive Cyclist Fit Calculator" published on or before Dec. 31, 2004 and printed from URL <http://www.competitivecyclist.com/docs/competitivecyclist/fitcal/road-fit.pdf>, 5 pages.*

"DIY Bike fitting—a ticket to cycling Utopia" written by Andy Choy, published on or before May 5, 2011, and printed from URL <http://web.archive.org/web/20111101085610/http://www.bikepro.com.au/diy-bike-fitting>, 8 pages.*

"Retul Fit System" review written by Matt Pacocha, published on or before Dec. 16, 2010, and printed from URL <http://www.bikeradarcom/us/gear/category/tools/cycling-tools/fitting-systems/product/review-retul-fit-system-42715/>, 5 pages.*

"Retül Total Bike Fit Solutions" published by RetulBikeFit to YouTube on or before Jul. 2, 2012, printed from URL <https://www.youtube.com/watch?v=C2Fq0D8S2LQ>, 1 page.*

"The Guru Experience Bike Fitting System" published by Bert's Bikes and Fitness on or before Mar. 29, 2013, printed from URL <https://www.youtube.com/watch?v=knQghyE_o60>, 1 page.*

"The Guru Experience" published on or before Jun. 8, 2013, printed from URL <http://web.archive.org/web/20130608064540/http://www.gurucycling.com/the-experience/>, 1 page.*

"BikeDynamics—Bike Fitting Specialists" published on or before Nov. 1, 2011 and printed from <http://web.archive.org/web/20111101162724/http://bikedynamics.co.uk/achesandpains.htm> 4 pages.*

"Find the Animal in You" published on or before Aug. 15, 2012 and printed from <http://web.archive.org/web/20120815032144/http://www.fizik.it/spineconcept>, 8 pages.*

"Are You Sitting Comfortably" written by Cycling Plus, published on or before May 16, 2011, printed from URL <http://www.bikeradar.com/us/gear/article/health-are-you-sitting-comfortably-30179/>, 6 pages.*

"An outline of the BG FIT program and how it can benefit cyclists worldwide, from the pro peloton to the weekend enthusiast", Specialized Bicycles BG FIT, Mar. 2009.

* cited by examiner

| Flexibility Level | Good | | |
|---|---|---|---|
| | competition | sport | comfort |
| Measurement Title | Road | Road | Road |
| Knee Angle Max | 148(153-143) | 148(153-143) | 148(153-143) |
| Hip Angle Min | 52(47-57) | 55(50-60) | 58(53-63) |
| Measurement Title | TT | TT | TT |
| Knee Angle Max | 145.5(148-143) | | |
| Hip Angle Min | 32(27-37) | | |
| Measurement Title | Tri | Tri | Tri |
| Knee Angle Max | 145.5(148-143) | 145.5(148-143) | |
| Hip Angle Min | 42(37-47) | 45(40-50) | |
| Measurement Title | MTB | MTB | MTB |
| Knee Angle Max | 148(153-143) | 148(153-143) | 148(153-143) |
| Hip Angle Min | 62(52-72) | 65(55-75) | 68(58-78) |
| Measurement Title | Touring | Touring | Touring |
| Knee Angle Max | | 145(150-140) | 145(150-140) |
| Hip Angle Min | | 63(53-73) | 66(56-76) |
| Measurement Title | CX | CX | CX |
| Knee Angle Max | XX | | |
| Hip Angle Min | YY | | |

FIG. 5

| Flexibility Level | Fair | | |
|---|---|---|---|
| | competition | sport | comfort |
| Measurement Title | Road | Road | Road |
| Knee Angle Max | 145(150-140) | 145(150-140) | 145(150-140) |
| Hip Angle Min | 57(52-62) | 60(55-65) | 63(58-68) |
| Measurement Title | TT | TT | TT |
| Knee Angle Max | 142.5(145-140) | | |
| Hip Angle Min | 37(32-42) | | |
| Measurement Title | Tri | Tri | Tri |
| Knee Angle Max | 142.5(145-140) | 142.5(145-140) | |
| Hip Angle Min | 47(42-52) | 50(45-55) | |
| Measurement Title | MTB | MTB | MTB |
| Knee Angle Max | 145(150-140) | 145(150-140) | 145(150-140) |
| Hip Angle Min | 67(57-77) | 70(60-80) | 73(63-83) |
| Measurement Title | Touring | Touring | Touring |
| Knee Angle Max | | 142(147-137) | 142(147-137) |
| Hip Angle Min | | 68(58-78) | 71(61-81) |
| Measurement Title | CX | CX | CX |
| Knee Angle Max | XX | | |
| Hip Angle Min | YY | | |

FIG. 6

| Flexibility Level | Stiff | | |
|---|---|---|---|
| | competition | sport | comfort |
| Measurement Title | Road | Road | Road |
| Knee Angle Max | 142(147-137) | 142(147-137) | 142(147-137) |
| Hip Angle Min | 59(54-64) | 62(57-67) | 65(60-70) |
| Measurement Title | TT | TT | TT |
| Knee Angle Max | 139.5(142-137) | | |
| Hip Angle Min | 39(34-44) | | |
| Measurement Title | Tri | Tri | Tri |
| Knee Angle Max | 139.5(142-137) | 139.5(142-137) | |
| Hip Angle Min | 49(44-54) | 52(47-57) | |
| Measurement Title | MTB | MTB | MTB |
| Knee Angle Max | 142(147-137) | 142(147-137) | 142(147-137) |
| Hip Angle Min | 69(59-79) | 73(62-82) | 75(65-85) |
| Measurement Title | Touring | Touring | Touring |
| Knee Angle Max | | 139(144-134) | 139(144-134) |
| Hip Angle Min | | 70(60-80) | 73(63-83) |
| Measurement Title | CX | CX | CX |
| Knee Angle Max | XX | | |
| Hip Angle Min | YY | | |

FIG. 7

| Measurement Title | Road | 64 |
|---|---|---|
| Armpit Angle | 77.5 | θ4 |
| Elbow Angle | XX | θ5 |
| First Deviation | -10 | S |
| Measurement Title | TT | |
| Armpit Angle | 75 | θ4 |
| Elbow Angle | 95 | θ5 |
| First Deviation | 55 | S |
| Measurement Title | Tri | |
| Armpit Angle | 75 | θ4 |
| Elbow Angle | 95 | θ5 |
| First Deviation | 55 | S |
| Measurement Title | MTB | |
| Armpit Angle | 70 | θ4 |
| Elbow Angle | XX | θ5 |
| First Deviation | XX | S |
| Measurement Title | Touring | |
| Armpit Angle | 69 | θ4 |
| Elbow Angle | XX | θ5 |
| First Deviation | XX | S |
| Measurement Title | CX | |
| Armpit Angle | XX | θ4 |
| Elbow Angle | XX | θ5 |
| First Deviation | XX | S |

FIG. 8

BICYCLE FITTING SYSTEM

BACKGROUND

1. Field of the Invention

The present invention generally relates to a bicycle fitting system. In particular, the present invention relates to a bicycle fitting system for a bicycle fitting.

2. Background Information

Conventional bicycle fitting systems measures rider body sizes of a rider, and adjusts bicycle components of a bicycle based on the rider body sizes. For example, a conventional bicycle fitting system utilizes a three-dimensional marker tracking system that detects markers attached to a rider body for measuring rider body sizes of the rider (see U.S. Patent Application Publication No. 2007/0142177 A1, for example).

SUMMARY

For the sake of rider's comfort and cycling performance while riding the bicycle, the bicycle components need to be properly adjusted for obtaining a suitable riding posture for the rider. However, it has been discovered that it is difficult to find a suitable riding posture of a rider since the suitable riding posture varies according to rider body characteristics, bicycle types, riding types or the like.

One object of the disclosure is to provide a bicycle fitting system with which a suitable position of a bicycle component can be obtained for each rider.

In accordance with a first aspect, a bicycle fitting system includes a controller programmed to determine whether a current rider position of a rider is appropriate based on a flexibility level of a rider body of the rider.

In accordance with a second aspect, the bicycle fitting system according to the first aspect further includes a motion capturing apparatus electrically connected to the controller. The controller is further programmed to determine the flexibility level using the motion capturing apparatus.

In accordance with a third aspect, with the bicycle fitting system according to the second aspect, the controller is further programmed to measure a plurality of rider body parameters of the rider body using the motion capturing apparatus while the rider is on a bicycle fitting equipment.

In accordance with a fourth aspect, with the bicycle fitting system according to the third aspect, the controller is further programmed to set a parameter range of one of the rider body parameters based on the flexibility level, and output a bicycle fitting information based on both the rider body parameters and the parameter range of the one of the rider body parameters.

In accordance with a fifth aspect, with the bicycle fitting system according to the fourth aspect, the bicycle fitting information indicates a bicycle component position of a bicycle component.

In accordance with a sixth aspect, with the bicycle fitting system according to the fourth aspect, the bicycle fitting information indicates whether the one of the rider body parameters falls within the parameter range of the one of the rider body parameters.

In accordance with a seventh aspect, with the bicycle fitting system according to the fourth aspect, the controller is further programmed to acquire category information indicative of at least one of a bicycle type and a riding type, and set the parameter range of the one of the rider body parameters based on the flexibility level and the category information.

In accordance with an eighth aspect, with the bicycle fitting system according to the fifth aspect, the controller is further programmed to determine a setting position of at least one of a bicycle seat and a bicycle handle as the bicycle component position.

In accordance with a ninth aspect, with the bicycle fitting system according to the fourth aspect, the controller is further programmed to determine a temporal bicycle component position of a bicycle component based on the rider body parameters in response to the one of the rider body parameters falling outside the parameter range of the one of the rider body parameters. The bicycle fitting equipment is adjusted based on the temporal bicycle component position.

In accordance with a tenth aspect, with the bicycle fitting system according to the fifth aspect, the controller is further programmed to output the bicycle component position on an output apparatus.

In accordance with an eleventh aspect, with the bicycle fitting system according to the tenth aspect, the controller is further programmed to acquire an initial bicycle component position of the bicycle component. The controller is further programmed to output the bicycle component position and the initial bicycle component position.

In accordance with a twelfth aspect, with the bicycle fitting system according to the fifth aspect, the controller is further programmed to determine an adjustment direction of the bicycle component and an adjustment amount of the bicycle component based on the bicycle component position. The controller is further programmed to output the adjustment direction and the adjustment amount on an output apparatus.

In accordance with a thirteenth aspect, with the bicycle fitting system according to the fourth aspect, the controller is further programmed to display an indicator with a first predetermined status in response to the one of the rider body parameters falling within the parameter range of the one of the rider body parameters on a display screen. The controller is further programmed to display the indicator with a second predetermined status in response to the one of the rider body parameters falling outside the parameter range of the one of the rider body parameters on the display screen. The second predetermined status is different from the first predetermined status.

BRIEF DESCRIPTION OF THE DRAWINGS

Referring now to the attached drawings which form a part of this original disclosure:

FIG. 5 is a schematic diagram of a part of a parameter range table storing parameter ranges of the rider body parameters in association with the flexibility levels, bicycle types, and riding types;

FIG. 6 is a schematic diagram of another part of the parameter range table storing the parameter ranges of the rider body parameters in association with the flexibility levels, the bicycle types, and the riding types;

FIG. 7 is a schematic diagram of yet another part of the parameter range table storing the parameter ranges of the rider body parameters in association with the flexibility levels, the bicycle types, and the riding types;

FIG. 8 is a schematic diagram of a preset parameter table storing predetermined values of the rider body parameters in association with the bicycle types;

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Figure 1:
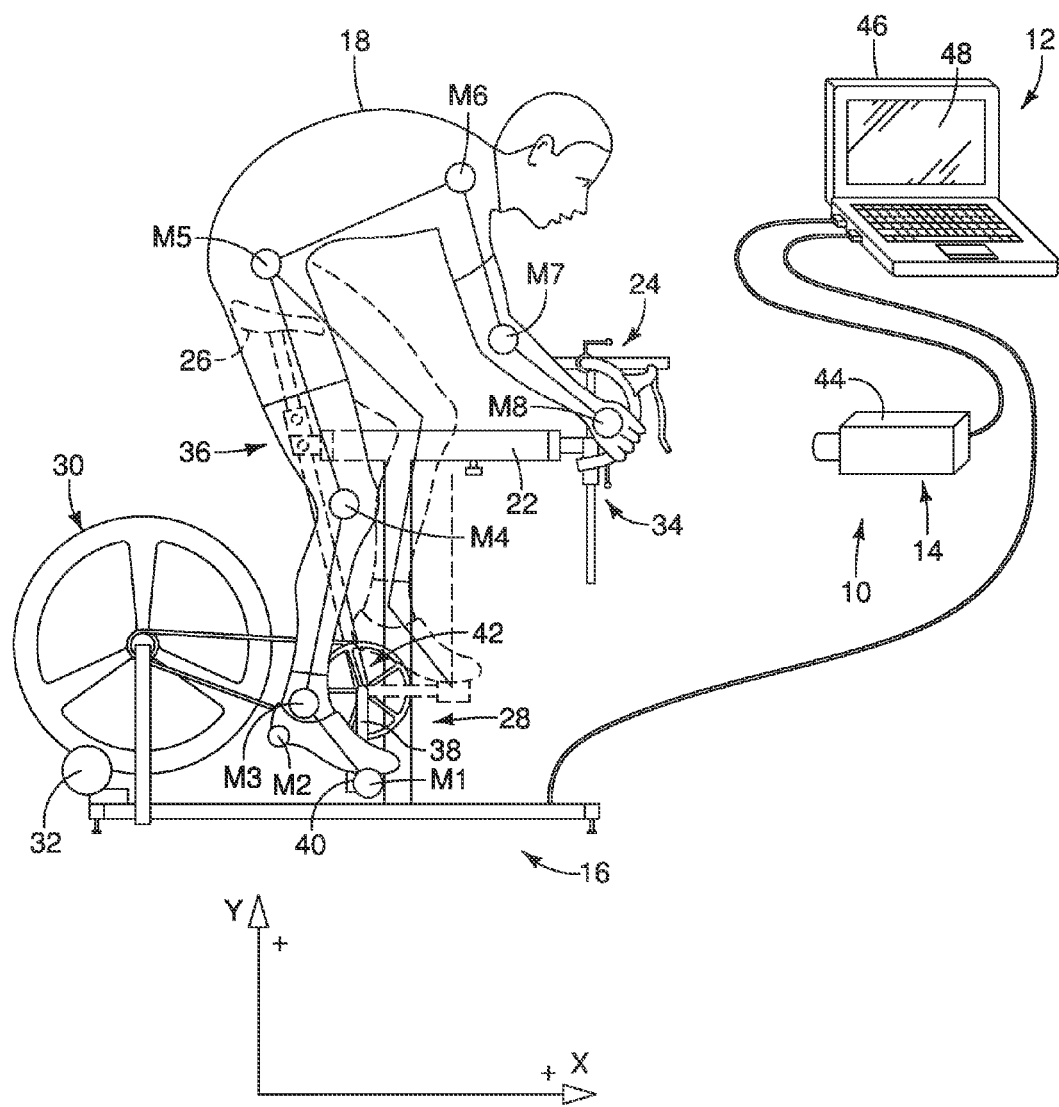
FIG. 1 is a schematic view of a bicycle fitting system in accordance with a first embodiment, illustrating a rider riding on a bicycle fitting equipment while a motion capturing apparatus detects LEDs attached to a rider body of the rider.

Referring initially to FIG. 1, a bicycle fitting system 10 is illustrated in accordance with a first embodiment. As illustrated in FIG. 1, the bicycle fitting system 10 includes a controller 12. The bicycle fitting system 10 also includes a motion capturing apparatus 14 electrically connected to the controller 12. In the illustrated embodiment, the bicycle fitting system 10 determines whether a current rider position of a rider is appropriate while the rider is riding on a bicycle fitting equipment 16. Specifically, with the bicycle fitting system 10, the controller 12 is programmed to measure a plurality of rider body parameters of a rider body 18 using the motion capturing apparatus 14 while the rider is on the bicycle fitting equipment 16. Furthermore, the controller 12 is further programmed to determine bicycle component positions of bicycle components. In the illustrated embodiment, the controller 12 determines a suitable seat position and a suitable handlebar position. However, the controller 12 can also be configured to determine bicycle component positions other than the suitable seat position and the suitable handlebar position. The configurations of the controller 12 will be explained later in detail.

The bicycle fitting equipment 16 is equipment that makes it possible to simulate a bicycle riding while remaining stationary. The bicycle fitting equipment 16 includes a stand or frame 22, a handlebar 24 (e.g., a bicycle handle), a seat or saddle 26 (e.g., a bicycle seat), a crank assembly 28, a rear wheel 30 and a resistance unit 32. The handlebar 24 and the seat 26 are adjustably coupled to the frame 22 in a conventional manner. The handlebar 24 and the seat 26 are adjustable with respect to the frame 22 in a horizontal direction X and in a vertical direction Y perpendicular to the horizontal direction X. Specifically, in the illustrated embodiment, the handlebar 24 is adjustably supported to the frame 22 by an adjustable handlebar support 34. The adjustable handlebar support 34 is operatively disposed between the frame 22 and the handlebar 24. The adjustable handlebar support 34 has a horizontal part horizontally slidable with respect to the frame 22, and a vertical part vertically slidable with respect to the horizontal part. The seat 26 is also adjustably supported by an adjustable seat support 36 in the horizontal direction X and in the vertical direction Y. In the illustrated embodiment, the handlebar 24 and the seat 26 are manually adjustable with respect to the frame 22. Specifically, the adjustable handlebar support 34 has scales indicative of current handlebar positions in the horizontal direction X and in the vertical direction Y, respectively, with respect to a reference position or origin of the frame 22. Also, the adjustable seat support 36 has scales indicative of current seat positions in the horizontal direction X and in the vertical direction Y, respectively, with respect to the reference position or origin of the frame 22. As mentioned above, in the illustrated embodiment, the handlebar 24 and the seat 26 are manually adjustable with respect to the frame 22. However, of course, the bicycle fitting equipment 16 can include an electrical drive unit for automatically and electrically adjusting the handlebar 24 and the seat 26 in the horizontal direction X and the vertical direction Y. Furthermore, the bicycle fitting equipment 16 can be electrically connected to the controller 12 to output adjustment data indicative of handlebar adjustment amounts in the horizontal direction X and in the vertical direction Y, and adjustment data indicative of seat adjustment amounts in the horizontal direction X and in the vertical direction Y. In particular, in this case, the adjustable handlebar support 34 has sensors to detect the handlebar adjustment amounts of the handlebar 24 with respect to the frame 22 in the horizontal direction X and in the vertical direction Y, and outputs the adjustment data indicative of the handlebar adjustment amounts to the controller 12. On the other hand, the adjustable seat support 36 has sensors to detect the seat adjustment amounts of the seat 26 with respect to the frame 22 in the horizontal direction X and in the vertical direction Y, and outputs the adjustment data indicative of the seat adjustment amounts to the controller 12.

The crank assembly 28 is rotatably supported to the frame 22 by a bottom bracket part. The crank assembly 28 has a pair of crank arms 38. Each of the crank arms 38 includes a pedal 40 that is mounted to the free end of a respective one of the crank arms 38. The crank arms 38 have inner ends fixed to opposite ends a crank axle 42, with the crank arms 38 extending in opposite radial directions from the crank axle 42. In the illustrated embodiment, the crank axle 42 has a center axis that defines the origin of an orthogonal coordinate system with axes extending in the horizontal direction X and in the vertical direction Y, respectively. In other words, the center axis of the crank axle 42 is perpendicular to the horizontal direction X and the vertical direction Y. The center axis of the crank axle 42 is a rotational axis, and coincident with a center axis of the bottom bracket.

The rear wheel 30 is rotatably supported to the frame 22. The rear wheel 30 is operatively coupled to the crank assembly 28 via a drive train that transmits pedaling force applied to the crank assembly 28 to the rear wheel 30 to rotate the rear wheel 30. The resistance unit 32 provides resistance on the rear wheel 30. The resistance unit 32 can be a conventional unit used in bicycle trainers or the like, such as a unit creating the resistance by a wind, a magnet, fluid or the like. The detailed configurations of the resistance unit 32 will be omitted for the sake of brevity. With this bicycle fitting equipment 16, the rider can simulate a bicycle riding while the rider is on the bicycle fitting equipment 16. However, for the purpose of measuring the rider positions, the bicycle fitting equipment 16 can be formed without the rear wheel 30 and the resistance unit 32. Furthermore, the bicycle fitting equipment 16 can be any other types of stationary bicycles (e.g., adjustable stationary cycling machines), or bicycle trainers that make it possible to ride a bicycle while it remains stationary.

The motion capturing apparatus 14 is configured to detect markers M1 to M8 attached near joints of the rider body 18 of the rider to identify positions of the rider body 18 and a bicycle riding posture of the rider body 18. The markers M1 to M8 are made by LEDs (Light Emitting Diodes), respectively, in this embodiment. Hereafter, in the illustrated embodiment, the markers M1 to M8 are referred to as LEDs M1 to M8, respectively. However, the markers M1 to M8 can be made by light sources other than the LEDs, reflectors or specific color members. The motion capturing apparatus 14 is also configured to output the detection results to the controller 12. In the illustrated embodiment, a conventional motion capturing apparatus can be used as the motion capturing apparatus 14. Thus, the detailed configurations of the motion capturing apparatus 14 will be omitted for the sake of brevity. In the illustrated embodiment, the motion capturing apparatus 14 has an image sensor or camera 44 that detects the LEDs M1 to M8. The LEDs M1 to M8 are powered and actuated electrically through a wiring (not shown), and actively illuminated. Alternatively, the LEDs M1 to M8 can be powered and actuated by batteries which are installed in housings of the LEDs M1 to M8, respectively. In other words, in the illustrated embodiment, the motion capturing apparatus 14 uses an active marker system for motion capture. However, any other types of motion capturing system, such as a system using an acoustic, inertial, magnetic or reflective markers, can be used as the motion capturing apparatus 14.

In the illustrated embodiment, the LEDs M1 to M8 are attached to the rider body 18. The attachments can be performed by a conventional means, such as a double-sided adhesive tape, a hook-and-loop fastener, an elastic band, or the like. The LEDs M1 to M8 are non-movably attached to the rider body 18 on the joints of the rider body 18 in a visible manner. In the illustrated embodiment, as shown in FIG. 1, the camera 44 of the motion capturing apparatus 14 detects the rider position by capturing images of the rider body 18 on the right side. Thus, the LEDs M1 to M8 are attached to the following locations on the right outside of the rider body 18. The LED M1 is located at a center between the thenar of a rider foot and the hypothenar of the rider foot as viewed from the right outside of the rider body 18. The LED M2 is located at the heel of the rider foot. The LED M3 is located at the malleous or ankle of the rider foot. The LED M4 is located at the knee joint of a rider leg. The LED M5 is located at the greater trochanter of the rider body 18. The LED M6 is located at the acromio of the rider body 18. The LED M7 is located at the elbow joint of a rider arm. The LED M8 is located at the radiocarpal jaw of the rider arm. The locations of the LEDs M1 to M8 are merely examples. Thus, the LEDs M1 to M8 can be attached to alternative locations from the above-mentioned locations. Furthermore, additional LEDs can be further used. In the illustrated embodiment, the LEDs M1 to M8 can be directly attached to the rider body 18 at locations where the rider body 18 is exposed. However, the LEDs M1 to M8 can also be attached on a surface of clothing, a sock, or a shoe at locations where the rider body 18 is not exposed.

The motion capturing apparatus 14 detects the LEDs M1 to M8 to determine the current rider position of the rider. Specifically, the camera 44 of the motion capturing apparatus 14 is electrically coupled to a computer system 46. The computer system 46 has a motion capturing software that calculates relative positions of the LEDs M1 to M8 (e.g., distances or directions between pairs selected from the LEDs M1 to M8) in the orthogonal coordinate system with the axes extending in the horizontal direction X and in the vertical direction Y, respectively, based on the captured images by the camera 44. Of course, alternatively, the computer system 46 can be configured to detect absolute positions or coordinates of the LEDs M1 to M8 in the orthogonal coordinate system with the axes extending in the horizontal direction X and in the vertical direction Y, respectively, based on the captured images by the camera 44. In the illustrated embodiment, the computer system 46 also forms the controller 12. However, of course, the motion capturing apparatus 14 can include a separate computer system that is electrically connected from the computer system 46 and that provides the calculated positions of the LEDs M1 to M8 to the computer system 46.

The computer system 46 forms the controller 12, and includes a microcomputer, a computer readable medium (e.g., memory, hard disk, etc.) with one or more executable control programs stored thereon or is communicable with such a computer readable medium in order to execute the control program(s). The computer system 46 also preferably includes other conventional components such as an input interface circuit, an output interface circuit, and storage devices such as a ROM (Read Only Memory) device and a RAM (Random Access Memory) device to store programming, data, calculations and/or results. Specifically, in the illustrated embodiment, the microcomputer of the computer system 46 forms the controller 12, and is programmed to send control commands to and/or receive information from the motion capturing apparatus 14, as explained above. It will be apparent to those skilled in the art from this disclosure that the precise structure and algorithms for the controller 12 can be any combination of hardware and software that will carry out the functions of the present disclosure. In the illustrated embodiment, the computer system 46 is illustrated as a laptop personal computer. However, the computer system 46 can be any other types of computer, such as a desktop computer, or a bicycle computer. The computer system 46 includes a display screen 48.

Referring now to FIGS. 2 to 14, the operation of the controller 12 will be described in detail. In the illustrated embodiment, the controller 12 is programmed to determine whether a current rider position of the rider is appropriate based on a flexibility level of the rider body 18 of the rider. Specifically, in the illustrated embodiment, the controller 12 determines whether the current rider position of the ride is appropriate while the rider is on the bicycle fitting equipment 16, and determines a suitable handlebar position of the handlebar 24 and a suitable seat position of the seat 26 for the rider when the current rider position of the rider matches with a predetermined condition described later.

Figure 2:
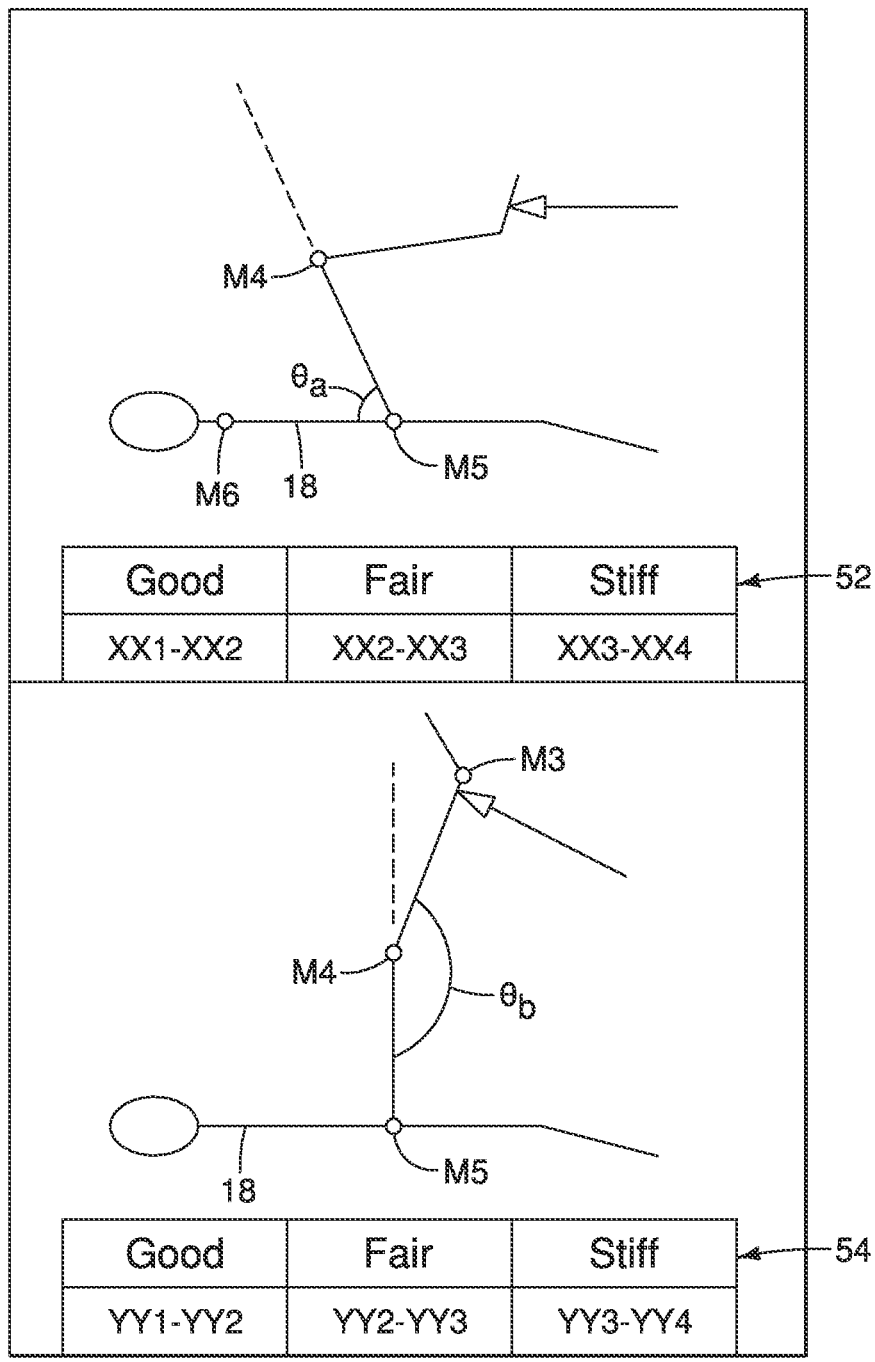
FIG. 2 is a schematic diagram illustrating measurements of flexibility levels of the rider body of the rider.

In the illustrated embodiment, as shown in FIG. 2, the controller 12 is further programmed to determine the flexibility level using the motion capturing apparatus 14. Specifically, in the illustrated embodiment, the controller 12 determines the flexibility level of the rider body 18 while the rider lies on the back. FIG. 2 illustrates a schematic image of the rider body 18. The controller 12 calculates a hip angle θa and a knee angle θb, respectively, based on the positions of the LEDs M3 to M5 and M6 determined by the motion capturing apparatus 14. The hip angle θa is calculated as an angle at the LED M5 enclosed by the lines from the LED M5 to the LED M4 and the LED M5 to the LED M6. For example, the hip angle θa is calculated while the rider pulls the thigh towards the chest as close as possible. The knee angle θb is calculated as an angle at the LED M4 enclosed by the lines from the LED M4 to the LED M5 and the LED M4 to the LED M3. For example, the knee angle θb is calculated while the rider straightens the knee as much as possible.

Then, a hip flexibility level of the hip angle θa is determined based on a hip flexibility table 52, while a knee flexibility level of the knee angle θb is determined on a knee flexibility table 54. In particular, in the illustrated embodiment, the hip flexibility level of the hip angle θa is classified into three categories, such as "Good" (e.g., a first category), "Fair" (e.g., a second category) and "Stiff" (e.g., a third category), according to the hip angle θa. In the illustrated embodiment, if the hip angle θa falls within a range of XX1 degree to XX2 degree, then the hip flexibility level is determined as "Good." Furthermore, if the hip angle θa falls within a range of XX2 degree to XX3 degree, then the hip flexibility level is determined as "Fair." Moreover, if the hip angle θa falls within a range of XX3 degree to XX4 degree, then the hip flexibility level is determined as "Stiff." On the other hand, in the illustrated embodiment, the knee flexibility level of the knee angle θb is classified into three categories, such as "Good", "Fair" and "Stiff", according to the knee angle θb. In the illustrated embodiment, if the knee angle θb falls within a range of YY1 degree to YY2 degree, then the knee flexibility level is determined as "Good." Furthermore, if the knee angle θb falls within a range of YY2 degree to YY3 degree, then the knee flexibility level is determined as "Fair." Moreover, if the knee angle θb falls within a range of YY3 degree to YY4 degree, then the knee flexibility level is determined as "Stiff." Then, the controller 12 stores the hip flexibility level and the knee flexibility level in a memory of the computer system 46. The specific values of the thresholds XX1, XX2, XX3, XX4, YY1, YY2, YY3, and YY4 are not described in the illustrated embodiment. However, it will be apparent to those skilled in the art from this disclosure that these thresholds can be experimentally predetermined. In the illustrated embodiment, the threshold XX1 is a smaller value than the threshold XX2, the threshold XX2 is a smaller value than the threshold XX3, and the threshold XX3 is a smaller value than the threshold XX4. Furthermore, the threshold YY1 is a larger value than the threshold YY2, the threshold YY2 is a larger value than the threshold YY3, and the threshold YY3 is a larger value than the threshold YY4.

In the illustrated embodiment, the hip flexibility level and the knee flexibility level are determined as the flexibility level of the present application. However, flexibility levels for other locations can be alternatively or additionally determined. Furthermore, in the illustrated embodiment, the hip and knee flexibility levels are classified into three categories, respectively. However, the number of categories can be less than or more than three. Furthermore, in the illustrated embodiment, the controller 12 determines the flexibility level of the rider body 18 while the rider lies on the back. However, the controller 12 can determine the flexibility level of the rider body 18 in a different manner, such as while the rider is standing. Alternatively, the controller 12 can merely obtain the flexibility level of the rider body 18 without measurements of the rider body 18 by the motion capturing apparatus 14. For example, if the flexibility level of the rider body 18 is measured in a conventional manner, then the flexibility level of the rider body 18 can be manually or electrically inputted to the computer system 46 of the controller 12.

Figure 3:
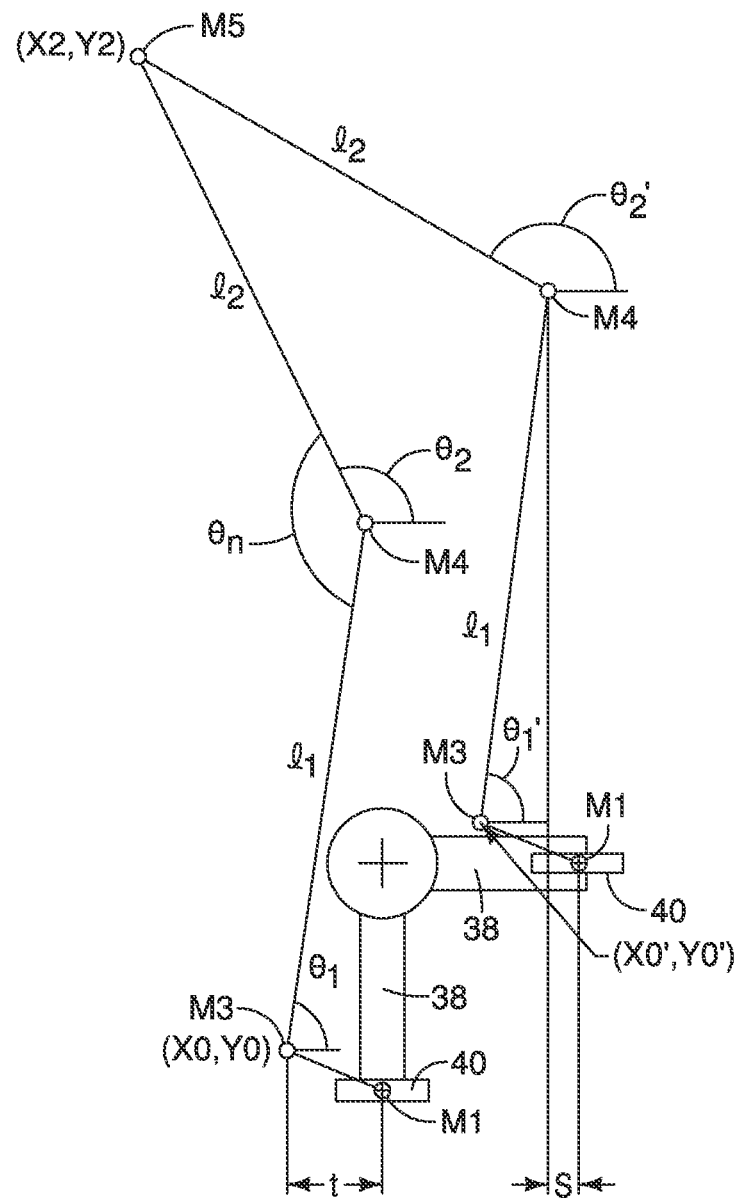
FIG. 3 is a schematic diagram illustrating rider body parameters of the rider body with respect to a crank assembly of the bicycle fitting stand.
Figure 4:
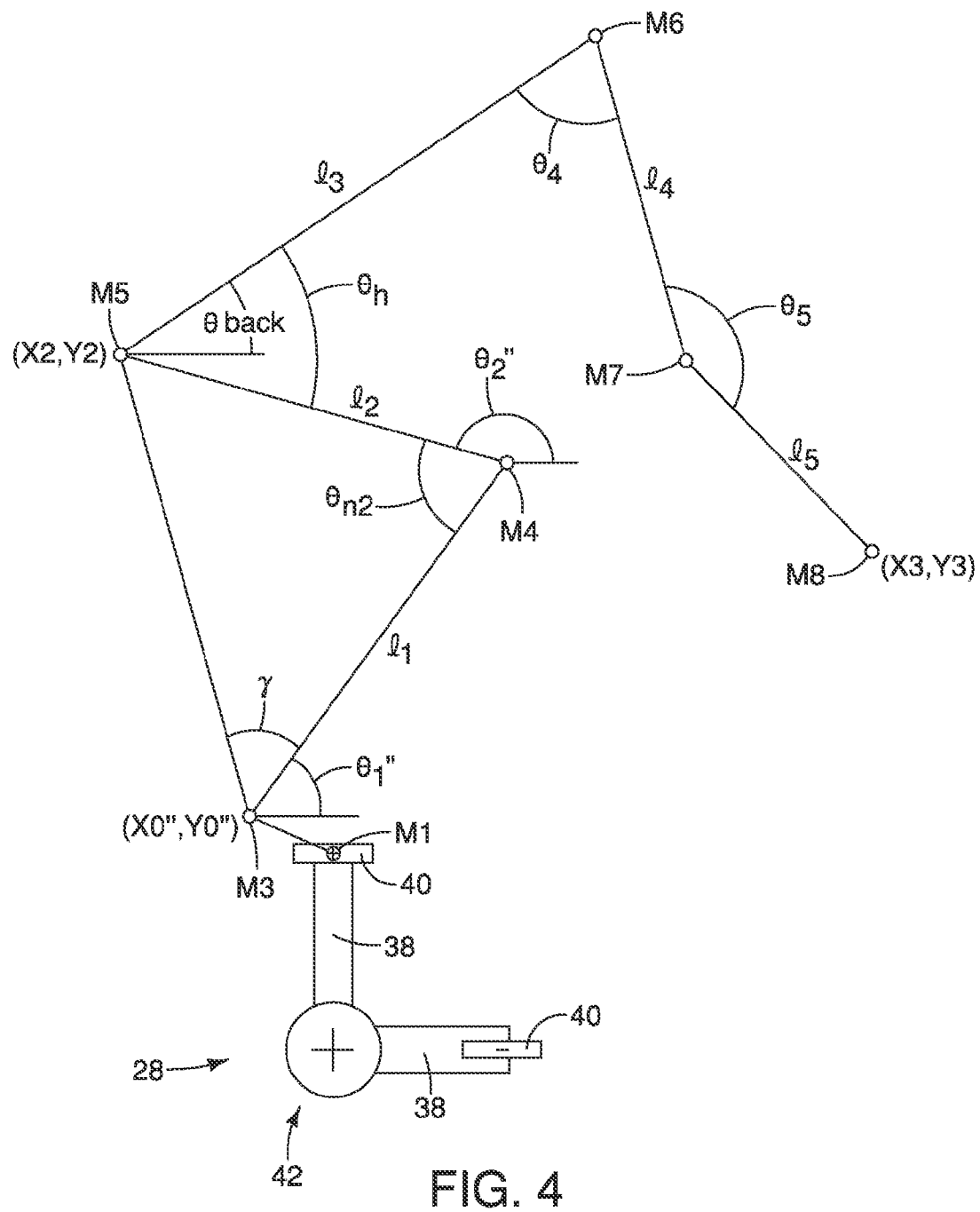
FIG. 4 is a schematic diagram illustrating rider body parameters of the rider body with respect to the crank assembly of the bicycle fitting stand.

Referring now to FIGS. 3 and 4, the rider body parameters of the rider body 18 will be described in detail. As mentioned above, the controller 12 is programmed to measure the rider body parameters of the rider body 18 using the motion capturing apparatus 14 while the rider is on the bicycle fitting equipment 16. In the illustrated embodiment, the controller 12 measures the rider body parameters of the rider body 18 based on the relative positions of the LEDs M1 to M8. The rider body parameters of the rider body 18 include a first length l1, a second length l2, a third length l3, a fourth length l4, a fifth length l5, a first deviation s, a second deviation t, a lower leg angle θ1, an upper leg angle θ2, a knee angle θn, a hip angle θh, an armpit angle θ4 and an elbow angle θ5. Specifically, the controller 12 measures the rider body parameters of the rider body 18 while the rider is on the bicycle fitting equipment 16, and is pedaling the crank assembly 28. In particular, the controller 12 starts measuring the rider body parameters of the rider body 18 once the pedaling or cadence becomes stable. In the illustrated embodiment, the controller 12 measures a set of the rider body parameters of the rider body 18 while the rider rotates the crank assembly 28 several times, e.g. ten times. However, the controller 12 can measure the set of the rider body parameters while the rider rotates the crank assembly 28 less than or more than ten times, as needed and/or desired.

As shown in FIGS. 3 and 4, the controller 12 measures the rider body parameters of the rider body 18 as follows. The first length l1 is defined as a distance between the LED M3 and the LED M4. The second length l2 is defined as a distance between the LED M4 and the LED M5. The third length l3 is defined as a distance between the LED M5 and the LED M6. The fourth length l4 is defined as a distance between the LED M6 and the LED M7. The fifth length l5 is defined as a distance between the LED M7 and the LED M8. The first deviation s is defined as a distance between the LED M1 and the LED M4 in the horizontal direction X when the crank arm 38 of the crank assembly 28 is horizontally oriented and the position of the LED M4 in the horizontal direction X has the maximum value. The second deviation t is defined as a distance between the LED M1 and the LED M3 in the horizontal direction X. In the illustrated embodiment, the controller 12 calculates an average value of the distances between the LED M3 and the LED M4 that are measured while the rider rotates the crank assembly 28 ten times, and determines the average value of the distances as the first length l1. Also, the controller 12 determines the second to fifth lengths l2 to l5, the first deviation s and the second deviation t in the same manner.

Furthermore, as shown in FIGS. 3 and 4, the lower leg angle θ1 is defined as an angle at the LED M3 enclosed by the horizontal line extending through the LED M3 and the line from the LED M3 to the LED M4 when the crank arm 38 of the crank assembly 28 is vertically oriented at the bottom dead center (i.e., the position of the LED M1 in the vertical direction Y has the minimum value). The upper leg angle θ2 is defined as an angle at the LED M4 enclosed by the horizontal line extending through the LED M4 and the line from the LED M4 to the LED M5 when the crank arm 38 of the crank assembly 28 is vertically oriented at the bottom dead center. The knee angle θn is defined as a maximum angle at the LED M4 enclosed by the lines from the LED M4 to the LED M5 and the LED M4 to the LED M3 during rotation of the crank assembly 28. Alternatively, the knee angle θn can be defined as an angle at the LED M4 enclosed by the lines from the LED M4 to the LED M5 and the LED M4 to the LED M3 when the crank arm 38 of the crank assembly 28 is vertically oriented at the bottom dead center. The hip angle θh is defined as a minimum angle at the LED M5 enclosed by the lines from the LED M5 to the LED M4 and the LED M5 to the LED M6 during rotation of the crank assembly 28. Alternatively, the hip angle θh can be defined as an angle at the LED M5 enclosed by the lines from the LED M5 to the LED M4 and the LED M5 to the LED M6 when the crank arm 38 of the crank assembly 28 is vertically oriented at the top dead center (i.e., the position of the LED M1 in the vertical direction Y has the maximum value). The armpit angle θ4 is defined as an angle at the LED M6 enclosed by the lines from the LED M6 to the LED M5 and the LED M6 to the LED M7. The elbow angle θ5 is defined as an angle at the LED M7 enclosed by the lines from the LED M7 to the LED M8 and the LED M7 to the LED M6. In the illustrated embodiment, the controller 12 calculates an average value of the angles at the LED M3 enclosed by the horizontal line extending through the LED M3 and the line from the LED M3 to the LED M4 when the crank arm 38 of the crank assembly 28 is vertically oriented at the bottom dead center that are measured while the rider rotates the crank assembly 28 ten times, and determines the average value of the angles as the lower leg angle θ1. Also, the controller 12 determines the upper leg angle θ2, the knee angle θn, the hip angle θh, the armpit angle θ4 and the elbow angle θ5 in the same manner.

As shown in FIGS. 5 to 7, the computer system 46 stores a parameter range table 62 for setting a parameter range of one of the rider body parameters in a memory or hard disc (not shown) of the computer system 46. In the illustrated embodiment, the controller 12 is further programmed to set the parameter range of the one of the rider body parameters based on the flexibility level. Specifically, the controller 12 is further programmed to acquire category information indicative of at least one of a bicycle type and a riding type, and set the parameter range of the one of the rider body parameters based on the flexibility level and the category information. First, the category information will be described in detail. As mentioned above, the category information indicates at least one of the bicycle type and the riding type. In the illustrated embodiment, the category information indicates both the bicycle type and the riding type. In the illustrated embodiment, the bicycle type indicates one of the following bicycle types: "Road," "TT," "Tri," "MTB" and "CX." The "Road" means a road bicycle, for example. The "TT" means a time trial bicycle or a racing bicycle for use in road time trial races, for example. The "Tri" means a triathlon bicycle, for example. The "MTB" means a mountain bicycle or a bicycle for off-road cycling. The "CX" means a cyclo-cross bicycle or a bicycle designed for a cyclo-cross race. The different bicycle types have different frame geometries and/or different bicycle components. In other words, the suitable riding posture for the same rider varies according to the bicycle types. In the illustrated embodiment, the bicycle fitting system 10 performs the bicycle fitting for the rider while taking these differences caused by the bicycle types into account. Furthermore, in the illustrated embodiment, the riding type indicates one of the following riding types: "competition," "sport" and "comfort." The "competition" means that the rider intends to seriously ride the bicycle for races. The "sport" means that the rider intends to ride the bicycle for fitness. The "comfort" means that the rider intends to casually ride the bicycle for fun. The suitable riding posture for the same rider varies according to the riding types. In the illustrated embodiment, the bicycle fitting system 10 performs the bicycle fitting for the rider while taking these differences caused by the riding types into account. The above classifications of the bicycle types and the riding types are merely provided as an example. Thus, the present application is not limited to these classifications of the bicycle types and the riding types. Specifically, in the illustrated embodiment, the bicycle types are classified into five. However, the number of the classification of the bicycle types can be less than or more than five. Furthermore, in the illustrated embodiment, the riding types are classified into three. However, the number of the classification of the riding types can be less than or more than three.

As shown in FIGS. 5 to 7, the parameter range table 62 stores or presets parameter ranges for the knee angle θn ("Knee Angle Max" in FIGS. 5 to 7) and the hip angle θh ("Hip Angle Min" in FIGS. 5 to 7) in association with the flexibility levels (e.g., "Good", "Fair" and "Stiff" in this embodiment), the bicycle types (e.g., "Road," "TT," "Tri," "MTB" and "CX" in this embodiment), and the riding types (e.g., "competition," "sport" and "comfort" in this embodiment). The controller 12 sets the parameter range for the knee angle θn according to the parameter range table 62 based on the knee flexibility level of the knee angle θb (FIG. 2), the bicycle type and the riding type. The controller 12 also sets the parameter range for the hip angle θh according to the parameter range table 62 based on the hip flexibility level of the hip angle θa (FIG. 2), the bicycle type and the riding type. In particular, the computer system 46 prompts the rider or an operator of the bicycle fitting system 10 to input the category information indicative of one of the bicycle types and one of the riding types. In response to receiving the category information, the computer system 46 stores the category information in the memory of the computer system 46. The controller 12 acquires the knee flexibility level, the hip flexibility level and the category information from the memory of the computer system 46, and sets the parameter ranges for the knee angle θn and the hip angle θh according to the parameter range table 62 based on the knee flexibility level, the hip flexibility level, the bicycle type and the riding type.

For example, if the rider selects the "Road" as the bicycle type and the "comfort" as the riding type, the knee flexibility level is "Stiff," and the hip flexibility level is "Good," then the controller 12 sets the parameter range for the knee angle θn as a range of 147-137 (degree) with a target value of 142 (degree) (see an encircled portion T11 in FIG. 7), and the parameter range for the hip angle θh as a range of 53-63 (degree) with a target value of 58 (degree) (see an encircled portion T12 in FIG. 5). In the illustrated embodiment, with the parameter range table 62, the target values are predetermined as mean values of the parameter ranges, respectively. These parameter ranges indicates the suitable ranges for the knee angle θn and the hip angle θh for the rider in view of the flexibility level of the rider body 18, the bicycle type and the riding type of the rider. In the illustrated embodiment, the parameter range table 62 is separately illustrated in FIGS. 5 to 7. However, in the illustrated embodiment, the parameter range table 62 is stored in the memory or hard disc of the computer system 46 as a single table. Of course, the parameter range table 62 can be stored in the memory or hard disc of the computer system 46 as separate tables. Furthermore, if the number of the classification of the bicycle type is one, then the parameter range table 62 can merely store the parameter ranges for the knee angle θn and the hip angle θh in association with the flexibility levels and the riding types. On the other hand, if the number of the classification of the riding type is one, then the parameter range table 62 can merely store the parameter ranges for the knee angle θn and the hip angle θh in association with the flexibility levels and the bicycle types. Furthermore, the values of the parameter ranges and the target values in the parameter range table 62 shown in FIGS. 5 to 7 are provided as an example. Thus, the values can be different values. Also, as shown in FIGS. 5 to 7, no parameter ranges are set for some combinations of the flexibility levels, the bicycle types, and the riding types, which are indicated using diagonal lines in the parameter range table 62. Furthermore, the values for some parameter ranges are indicated as "XX" or "YY" in FIGS. 5 to 7. Although the specific values of the "XX" or the "YY" are not described in the illustrated embodiment, it will be apparent to those skilled in the art from this disclosure that these thresholds can be experimentally predetermined.

Figure 9:
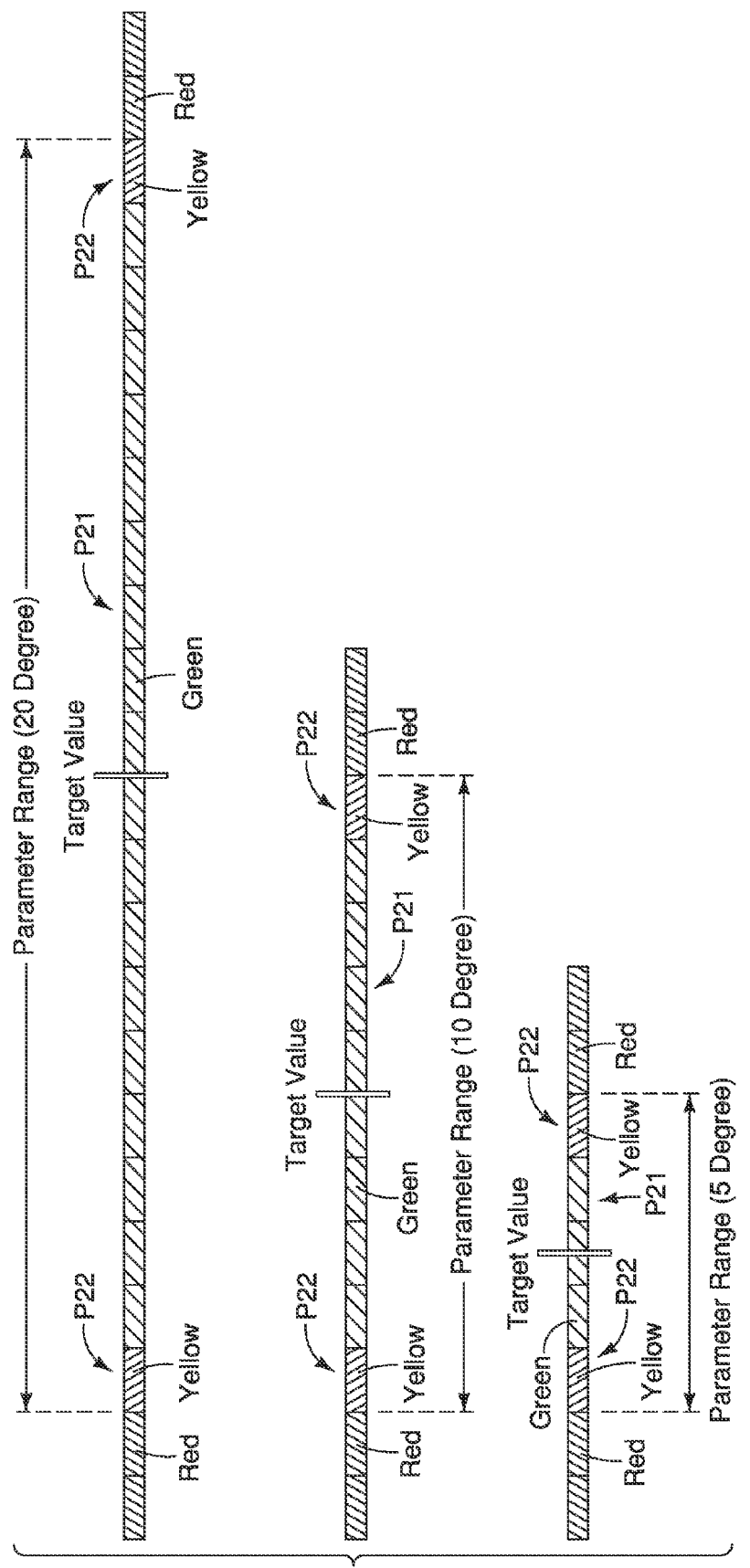
FIG. 9 is a schematic diagram illustrating determination of an indicator status of an indicator indicative of a status of a current rider position.
Figure 10:
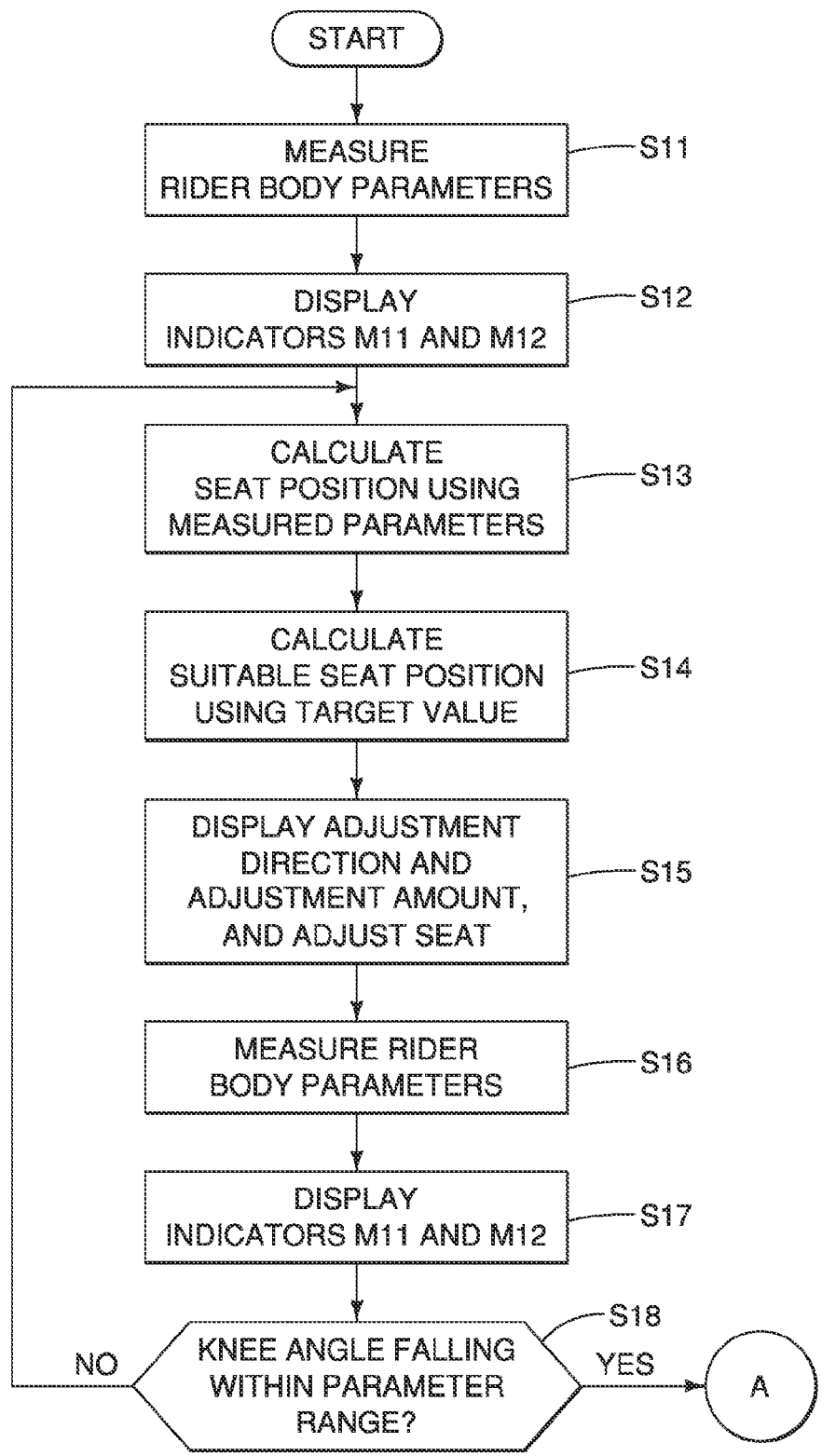
FIG. 10 is a flowchart of a suitable seat position calculation of a bicycle fitting method in accordance with the first embodiment.
Figure 11:
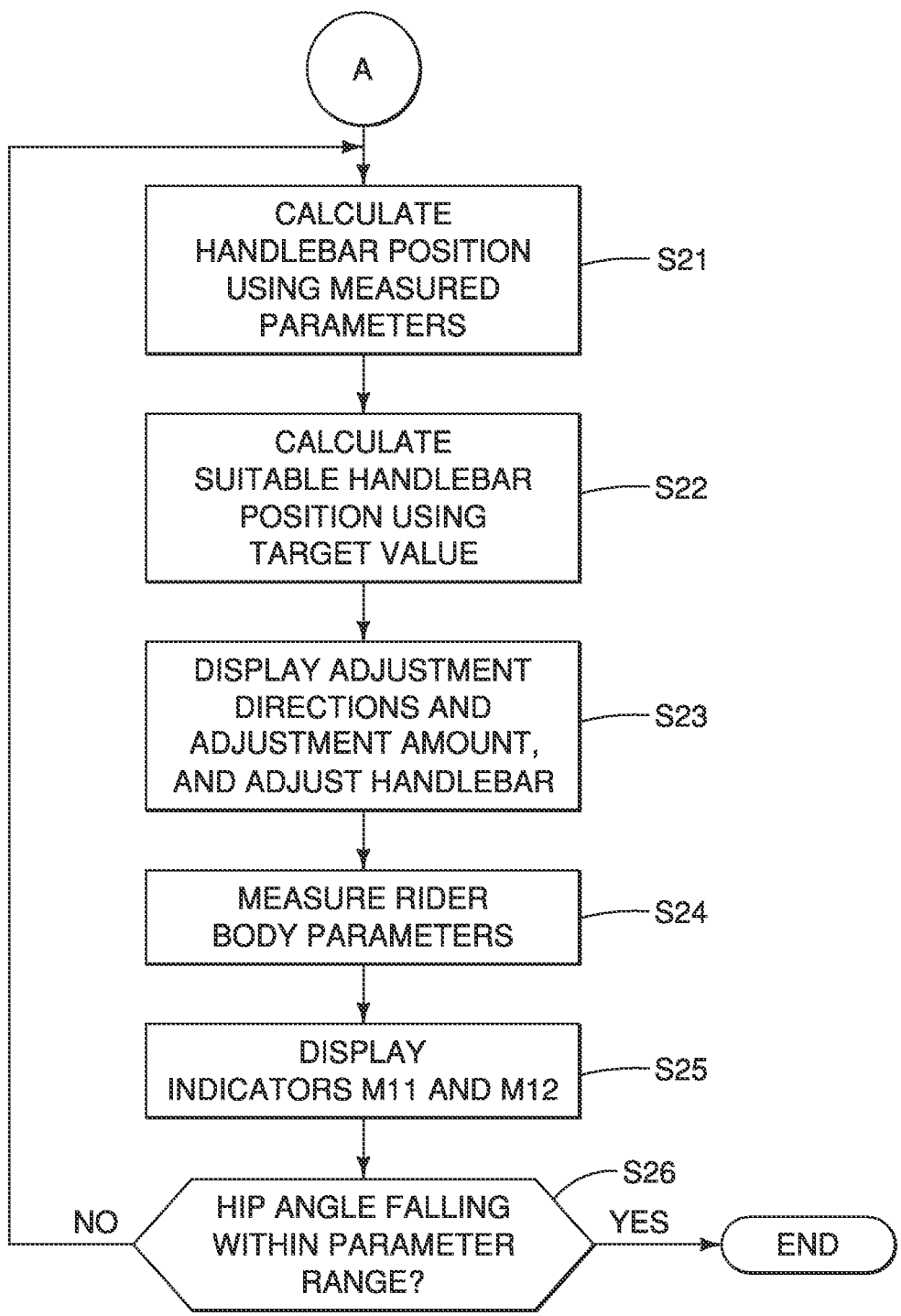
FIG. 11 is a flowchart of a suitable handlebar position calculation of the bicycle fitting method in accordance with the first embodiment.

Referring now to FIGS. 8 to 14, the bicycle fitting process or method performed by the controller 12 will be further described in detail. In the illustrated embodiment, the controller 12 is further programmed to determine the suitable seat position of the seat 26 and the suitable handlebar position of the handlebar 24. In other words, the controller 12 is further programmed to determine the suitable seat position and the suitable handlebar position (e.g., a setting position of at least one of a bicycle seat and a bicycle handle) as a bicycle component position of a bicycle component. FIGS. 10 and 11 are flowcharts of the bicycle fitting process for determining the suitable seat position of the seat 26 and the suitable handlebar position of the handlebar 24. Before performing the process shown in FIGS. 10 and 11, the controller 12 acquires the flexibility level of the rider body 18 and the category information indicative of the bicycle type and the riding type in a manner described above. As shown in FIG. 10, the controller 12 measures a set of the rider body parameters of the rider body 18 while the rider rotates the crank assembly 28 ten times (step S11 in FIG. 10). As mentioned above, the controller 12 measures the first length l1, the second length l2, the third length l3, the fourth length l4, the fifth length l5, the first deviation s, the second deviation t, the lower leg angle θ1, the upper leg angle θ2, the knee angle θn, the hip angle θh, the armpit angle θ4 and the elbow angle θ5 as the rider body parameters of the rider body 18.

Figure 12:
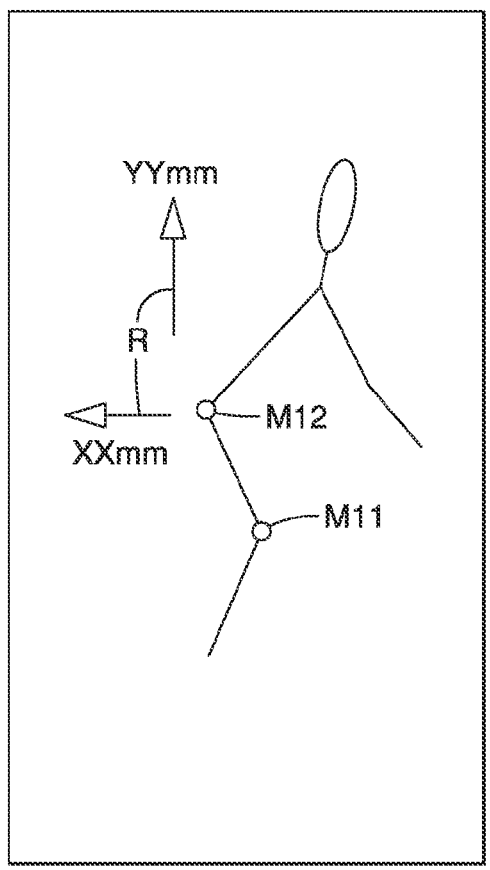
FIG. 12 is a schematic diagram of an display image displayed on a display screen, the display image showing an adjustment direction of the seat position and an adjustment amount of the seat position.

As shown in FIG. 10, in step S12, the controller 12 determines whether the current rider position of the rider is appropriate based on the flexibility level of the rider body 18 of the rider. In particular, in the illustrated embodiment, the controller 12 determines whether the measured knee angle θn measured in step S11 falls within the parameter range for the knee angle θn that has been determined using the parameter range table 62 based on the knee flexibility level of the knee angle θb (FIG. 2), the bicycle type and the riding type. Furthermore, the controller 12 also determines whether the measured hip angle θh measured in step S11 falls within the parameter range for the hip angle θh that has been determined using the parameter range table 62 based on the hip flexibility level of the hip angle θa (FIG. 2), the bicycle type and the riding type. Then, the controller 12 outputs a bicycle fitting information on the display screen 48 of the computer system 46 (step S12 in FIG. 10). Specifically, as shown in FIG. 12, the controller 12 output the bicycle fitting information as indicators M11 and M12. FIG. 12 is a graphical output on the computer system 46. The indicators M11 and M12 are displayed at locations corresponding to the LEDs M4 and M5, respectively. The indicator M11 indicates whether the measured knee angle θn falls within the parameter range for the knee angle θn, while the indicator M12 indicates whether the measured hip angle θh falls within the parameter range for the hip angle θh.

In particular, in the illustrated embodiment, as shown in FIGS. 9 and 12, the indicator M11 is displayed in a first color, such as green when the measured knee angle θn falls within a center (most suitable) portion P21 of the parameter range for the knee angle θn. The indicator M11 is displayed in a second color, such as yellow when the measured knee angle θn falls within edge portions P22 of the parameter range for the knee angle θn. The indicator M11 is displayed in a third color, such as red when the measured knee angle θn falls outside the parameter range for the knee angle θn. Furthermore, in the illustrated embodiment, as shown in FIGS. 9 and 12, the indicator M12 is displayed in the first color, such as green when the measured hip angle θh falls within the center portion P21 of the parameter range for the hip angle θh. The indicator M12 is displayed in the second color, such as yellow when the measured hip angle θh falls within the edge portions P22 of the parameter range for the hip angle θh. The indicator M12 is displayed in the third color, such as red when the measured hip angle θh falls outside the parameter range for the hip angle θh. The first color, the second color and the third color are different colors, respectively, in the illustrated embodiment. Specifically, in the illustrated embodiment, as illustrated in FIG. 9, the edge portions P22 of the parameter range are set as 1 degree width from the minimum and maximum value of the parameter range, respectively, while the center portion P21 of the parameter range is defined between the edge portions P22 of the parameter range. However, these settings can be different setting as needed and/or desired. Specifically, if the parameter range has 20 degree width, then the center portion P21 is set as a range of ±9 degree with respect to the target value and the edge portions P22 are set as outside portions of the center portion P21 within the parameter range. If the parameter range has 10 degree width, then the center portion P21 is set as a range of ±4 degree with respect to the target value and the edge portions P22 are set as outside portions of the center portion P21 within the parameter range. Furthermore, if the parameter range has 5 degree width, then the center portion P21 is set as a range of ±1.5 degree with respect to the target value and the edge portions P22 are set as outside portions of the center portion P21 within the parameter range.

Therefore, in the illustrated embodiment, the controller 12 is further programmed to output the indicators M11 and M12 (e.g., the bicycle fitting information) based on both the rider body parameters and the parameter ranges of the rider body parameters. Furthermore, the indicators M11 and M12 (e.g., the bicycle fitting information) indicate whether the rider body parameters fall within the parameter ranges of the rider body parameters. Moreover, the controller 12 is further programmed to display the indicators M11 and M12 with a first predetermined status (in green or yellow), respectively, in response to the rider body parameters falling within the parameter ranges of the rider body parameters on the display screen 48, respectively. The controller 12 is further programmed to display the indicators M11 and M12 with a second predetermined status (in red), respectively, in response to the rider body parameters falling outside the parameter ranges of the rider body parameters on the display screen 48, respectively. The second predetermined status is different from the first predetermined status. In the illustrated embodiment, the indicators M11 and M12 are displayed by changing colors to indicate whether the knee angle θn and the hip angle θh fall within the parameter ranges, respectively. Alternatively, the indicators M11 and M12 can be displayed by changing status of the indicators M11 and M12 to indicate whether the knee angle θn and the hip angle θh fall within the parameter ranges, respectively. For example, the indicators M11 and M12 can be displayed by changing shape, brightness, line-style or dash-style of the indicators M11 and M12, or by flashing on and off the indicators M11 and M12 to indicate whether the knee angle θn and the hip angle θh fall within the parameter ranges, respectively. Furthermore, in the illustrated embodiment, the indicators M11 and M12 are displayed in green, yellow or red. However, the indicators M11 and M12 can be displayed in only two colors, or in more than three colors according to the determination result.

Next, as shown in step S13 in FIG. 10, the controller 12 calculates the position (X2, Y2) of the seat 26 (the LED M5) with respect to the position (X0, Y0) of the LED M3 using the measured rider body parameters of the rider body 18, such as the first length l1, the second length l2, the first deviation s, the second deviation t, the lower leg angle θ1, the upper leg angle θ2, the knee angle θn, for example. For example, as shown in FIG. 3, the position (X2, Y2) of the seat 26 with respect to the position (X0, Y0) of the LED M3 is calculated based on Equations (18) and (19) below using measured rider body parameters of the rider body 18 measured in step S11 (or S16). Equations (18) and (19) will be described in detail later. In the illustrated embodiment, the position (X0, Y0) of the LED M3 is used as a reference position to calculate the relative position (X2, Y2) of the seat 26. Thus, the position (X0, Y0) of the LED M3 can be set as (0, 0). In the illustrated embodiment, the calculated position (X2, Y2) that is calculated for the first time after starting the bicycle fitting process is stored in the memory of the computer system 46 as an initial seat position.

Furthermore, the controller 12 determines the suitable seat position (X2, Y2) of the seat 26 using the target value for the knee angle θn (step S14 in FIG. 10). The target value for the knee angle θn has been determined using the parameter range table 62 based on the knee flexibility level of the knee angle θb (FIG. 2), the bicycle type and the riding type.

Referring now to FIG. 3, determination of the suitable seat position (X2, Y2) of the seat 26 for the rider by the controller 12 will be described in detail. As shown in FIG. 3, the seat position (X2, Y2) is expressed using the first length l1, the second length l2, the lower leg angle θ1 and the upper leg angle θ2 according to the following Equations (1) and (2).

$$X_2 = X_0 + l_1 \cos\theta_1 + l_2 \cos\theta_2 \quad (1)$$

$$Y_2 = Y_0 + l_1 \sin\theta_1 + l_2 \sin\theta_2 \quad (2)$$

Here, (X0, Y0) indicates the position of the LED 3 when the crank arm 38 of the crank assembly 28 is vertically oriented at the bottom dead center. The position (X0, Y0) of the LED 3 is used as a reference for the determination of the suitable seat position (X2, Y2).

The knee angle θn is expressed according to the following Equation (3).

$$\theta_n = \theta_1 + 180 - \theta_2 \quad (3)$$

On the other hand, the seat position (X2, Y2) can also be expressed according to the following Equations (4) and (5).

$$X_2 = X_0' + l_1 \cos\theta_1' + l_2 \cos\theta_2' \quad (4)$$

$$Y_2 = Y_0' + l_1 \sin\theta_1' + l_2 \sin\theta_2' \quad (5)$$

Here, (X0', Y0') indicates the position of the LED 3 when the crank arm 38 of the crank assembly 28 is horizontally oriented and forwardly extends from the crank axle 42 in the horizontal direction X. Furthermore, a lower leg angle θ1' is defined as an angle at the LED M3 enclosed by the horizontal line extending through the LED M3 and the line from the LED M3 to the LED M4 when the crank arm 38 of the crank assembly 28 is horizontally oriented and forwardly extends from the crank axle 42 in the horizontal direction X. Moreover, an upper leg angle θ2' is defined as an angle at the LED M4 enclosed by the horizontal line extending through the LED M4 and the line from the LED M4 to the LED M5 when the crank arm 38 of the crank assembly 28 is horizontally oriented and forwardly extends from the crank axle 42 in the horizontal direction X.

Furthermore, in regards to the lower leg angle θ1', the relationship expressed by the following Equation (6) is established using the first deviation s and the second deviation t.

$$X_0' + t + s = X_0' + l_1 \cos\theta_1' \quad (6)$$

Thus, the lower leg angle θ1' can be calculated based on Equation (6) as expressed in the following Equation (7).

$$l_1 \cos\theta_1' = s + t \quad (7)$$

$$\cos\theta_1' = \frac{s+t}{l_1}$$

$$\therefore \theta_1' = \cos^{-1}\frac{s+t}{l_1}$$

Furthermore, in regards to the positions (X0, Y0) and (X0', Y0'), the relationship expressed by the following Equations are established: X0'=X0+r; and Y0'=Y0+r. Here, r is a crank arm length of the crank arm 38 measured or defined between the center axis of the crank axle 42 (e.g., a crank axis) and a pedal axis of the pedal 40.

Furthermore, based on Equation (1), the relationship expressed by the following Equation (8) is established.

$$X_2 - X_0 = l_1 \cos\theta_1 + l_2 \cos\theta_2$$

$$\therefore (l_1 \cos\theta_1 + l_2 \cos\theta_2)^2 = (X_2 - X_0)^2$$

$$\therefore l_1^2 \cos^2\theta_1 + l_2^2 \cos^2\theta_2 + 2l_1 l_2 \cos\theta_1 \cos\theta_2 = (X_2 - X_0)^2 \quad (8)$$

Moreover, based on Equation (2), the relationship expressed by the following Equation (9) is established.

$$Y_2 - Y_0 = l_1 \sin\theta_1 + l_2 \sin\theta_2$$

$$\therefore (l_1 \sin\theta_1 + l_2 \sin\theta_2)^2 = (Y_2 - Y_0)^2$$

$$\therefore l_1^2 \sin^2\theta_1 + l_2^2 \sin^2\theta_2 + 2l_1 l_2 \sin\theta_1 \sin\theta_2 = (Y_2 - Y_0)^2 \quad (9)$$

By adding Equation (9) to Equation (8), the relationships expressed by the following Equations (10) and (11) are established.

$$l_1^2 + l_2^2 + 2l_1 l_2 (\cos\theta_1 \cos\theta_2 + \sin\theta_1 \sin\theta_2) = (X_2 - X_0)^2 + (Y_2 - Y_0)^2 \quad (10)$$

$$l_1^2 + l_2^2 + 2l_1 l_2 \cos(\theta_1 - \theta_2) = (X_2 - X_0)^2 + (Y_2 - Y_0)^2 \quad (11)$$

Based on Equations (3) and (11), the relationship expressed by the following Equation (12) is established.

$$l_1^2 + l_2^2 + 2l_1 l_2 \cos(\theta_n - 180) = (X_2 - X_0)^2 + (Y_2 - Y_0)^2 \quad (12)$$

Based on Equation (4), the relationship expressed by the following Equations are established.

$$X_0 + r + l_1 \cos\theta_1' + l_2 \cos\theta_2' = X_2$$

$$(r + l_1 \cos\theta_1') + l_2 \cos\theta_2' = X_2 - X_0$$

By multiplying each side by itself, the relationship expressed by the following Equation (13) is established.

$$(r + l_1 \cos\theta_1')^2 + l_2^2 \cos^2\theta_2' + 2l_2(r + l_1 \cos\theta_1')\cos\theta_2' = (X_2 - X_0)^2 \quad (13)$$

Furthermore, based on Equation (5), the relationships expressed by the following Equations are established.

$$Y_0 + r + l_1 \sin\theta_1' + l_2 \sin\theta_2' = Y_2$$

$$(r + l_1 \sin\theta_1') + l_2 \sin\theta_2' = Y_2 - Y_0$$

By multiplying each side by itself, the relationship expressed by the following Equation (14) is established.

$$(r + l_1 \sin\theta_1')^2 + l_2^2 \sin^2\theta_2' + 2l_2(r + l_1 \sin\theta_1')\sin\theta_2' = (Y_2 - Y_0)^2 \quad (14)$$

By adding Equation (14) to Equation (13), and by setting (r+l1 cos θ1') as A and (r+l1 sin θ1') as B, the relationships expressed by the following Equations (15) and (16) are established.

$$A^2 + B^2 + l_2^2 + 2l_2(A\cos\theta_2' + B\sin\theta_2') = (X_2 - X_0)^2 + (Y_2 - Y_0)^2 \quad (15)$$

$$A^2 + B^2 + l_2^2 + 2l_2\sqrt{A^2 + B^2}\sin\left(\theta_2' + \tan^{-1}\frac{A}{B}\right) = \quad (16)$$
$$(X_2 - X_0)^2 + (Y_2 - Y_0)^2$$

Furthermore, based on Equations (12) and (16), the relationship expressed by the following Equation (17) is established.

$$l_1^2 + l_2^2 + 2l_1l_2\cos(\theta_n - 180) = \quad (17)$$
$$A^2 + B^2 + l_2^2 + 2l_2\sqrt{A^2 + B^2}\sin\left(\theta_2' + \tan^{-1}\frac{A}{B}\right)$$
$$\frac{l_1^2 + 2l_1l_2\cos(\theta_n - 180) - A^2 - B^2}{2l_2\sqrt{A^2 + B^2}} = \sin\left(\theta_2' + \tan^{-1}\frac{A}{B}\right)$$
$$\therefore \theta_2' = \mathrm{Sin}^{-1}\left\{\frac{l_1^2 + 2l_1l_2\cos(\theta_n - 180) - A^2 - B^2}{2l_2\sqrt{A^2 + B^2}}\right\} \cdot \mathrm{Tan}^{-1}\frac{A}{B}$$

With this Equation (17), the upper leg angle $\theta_2'$ can be calculated using the knee angle $\theta_n$ as a parameter.

Moreover, based on the Equations (7) and (17), the lower leg angle $\theta_1'$ can also be calculated. Accordingly, the seat position (X2, Y2) can be calculated by the following Equations (18) and (19).

$$X_2 = X_0 + r + l_1\cos\theta_1' + l_2\cos\theta_2' \quad (18)$$

$$Y_2 = Y_0 + r + l_1\sin\theta_1' + l_2\sin\theta_2' \quad (19)$$

In the illustrated embodiment, the controller 12 calculates the suitable seat position (X2, Y2) based on the above-mentioned Equations (18) and (19). Specifically, the controller 12 calculates the lower leg angle $\theta_1'$ based on Equation (7) using the first deviation s, the second deviation t, and the first length l1. In the illustrated embodiment, the controller 12 calculates the lower leg angle $\theta_1'$ based on Equation (7) using the measured values of the second deviation t and first length l1 that have been measured as explained above, and a preset value of the first deviation s. As shown in FIG. 8, the computer system 46 stores a preset parameter table 64 for presetting preset parameters of the armpit angle $\theta_4$, the elbow angle $\theta_5$ and the first deviation s in a memory or hard disc (not shown) of the computer system 46. In particular, the preset parameter table 64 stores or presets the preset parameters for the armpit angle $\theta_4$, the elbow angle $\theta_5$ and the first deviation s in association with the bicycle types (e.g., "Road," "TT," "Tri," "MTB" and "CX" in this embodiment). The controller 12 sets the preset parameters for the armpit angle $\theta_4$, the elbow angle $\theta_5$ and the first deviation s based on the bicycle type of the category information inputted by the rider or the operator of the bicycle fitting system 10 to the computer system 46. In the illustrated embodiment, the controller 12 calculates Equation (7) using the preset value of the first deviation s. However, alternatively, the controller 12 can calculate Equation (7) using a measured value of the first deviation s. In the illustrated embodiment, as shown in FIG. 8, some of the preset parameters are indicated as "XX". Although the specific values of the "XX" are not described in the illustrated embodiment, it will be apparent to those skilled in the art from this disclosure that these thresholds can be experimentally predetermined.

The controller 12 further calculates the upper leg angle $\theta_2'$ based on Equation (17) using the first length l1, the second length l2, the crank arm length r, the lower leg angle $\theta_1'$ and the knee angle $\theta_n$. In the illustrated embodiment, the controller 12 calculates the upper leg angle $\theta_2'$ based on Equation (17) using the measured values of the first length l1 and the second length l2 that have been measured as explained above, the preset value of the crank arm length r, the calculated value of the lower leg angle $\theta_1'$ that has been calculated based on Equation (7), and the preset target value of the knee angle $\theta_n$. The preset target value of the knee angle $\theta_n$ is determined based on the parameter range table 62 shown in FIGS. 5 to 7 according to the knee flexibility level, the bicycle type and the riding type (i.e., the flexibility level of the rider body 18 and the category information).

Then, the controller 12 further calculates the suitable seat position (X2, Y2) based on the above-mentioned Equations (18) and (19) using the position (X0, Y0) of the LED M3, the crank arm length r, the first length l1, the second length l2, the lower leg angle $\theta_1'$ and the upper leg angle $\theta_2'$. In the illustrated embodiment, the controller 12 calculates the seat position (X2, Y2) based on the above-mentioned Equations (18) and (19) using the measured values of the first length l1 and the second length l2 that have been measured as explained above, the preset value of the crank arm length r, and the calculated values of the lower leg angle $\theta_1'$ and the upper leg angle $\theta_2'$ that have been calculated based on Equations (7) and (17). Furthermore, in the illustrated embodiment, the position (X0, Y0) of the LED M3 is used as a reference position to calculate the suitable seat position (X2, Y2) of the seat 26. Thus, the position (X0, Y0) of the LED M3 can be set as (0, 0).

Next, as shown in FIG. 12, the controller 12 outputs adjustment directions of the seat 26 and adjustment amounts of the seat 26 on the display screen 48 of the computer system 46 (step S15 in FIG. 10). Specifically, the controller 12 is further programmed to determine the adjustment directions of the seat 26 (e.g., the bicycle component) and the adjustment amounts of the seat 26 (e.g., the bicycle component) based on the suitable seat position (X2, Y2) (e.g., the bicycle component position). Specifically, in the illustrated embodiment, the controller 12 calculates the deviation between the position (X2, Y2) of the seat 26 calculated in step S13 and the suitable seat position (X2, Y2) of the seat 26 calculated in step S14. Specifically, the controller 12 subtract the position (X2, Y2) of the seat 26 calculated in step S13 from the suitable seat position (X2, Y2) of the seat 26 calculated in step S14 to obtain the adjustment directions of the seat 26 and the adjustment amounts of the seat 26 in the horizontal direction X and in the vertical direction Y. Then, as shown in FIG. 12, the controller 12 displays arrows R indicative of the adjustment directions of the seat 26 together with the adjustment amounts of the seat 26. In other words, the controller 12 is further programmed to output the adjustment directions and the adjustment amounts on the display screen 48 (e.g., the output apparatus). In the illustrated embodiment, the indicators M11 and M12, the adjustment directions and the adjustment amounts are displayed in the same display image as shown in FIG. 12. However, alternatively, the indicators M11 and M12, the adjustment directions and the adjustment amounts can be displayed in different display images, respectively.

The rider or the operator of the bicycle fitting system 10 adjusts the seat 26 with respect to the frame 22 according to the graphic image displayed on the display screen 48. While adjusting the seat 26 with respect to the frame 22, the bicycle fitting equipment 16 can output the adjustment data indicative of the actual seat adjustment amounts to the controller 12 in the horizontal direction X and in the vertical direction Y as ($\Delta x1$, $\Delta y1$). The controller 12 further outputs the adjustment directions of the seat 26 and the adjustment amounts of the seat 26 according to the seat adjustment amounts (Δx1, Δy1) from the bicycle fitting equipment 16. Specifically, if the seat adjustment amounts (Δx1, Δy1) from the bicycle fitting equipment 16 match with the adjustment amounts calculated in step S15, then the arrows R on the display screen 48 disappear to notify that the adjustment of the seat 26 with respect to the frame 22 has been completed.

Next, the controller 12 measures the set of the rider body parameters of the rider body 18 while the rider rotates the crank assembly 28 ten times in the same manner as step S11 (step S16 in FIG. 10).

As shown in FIG. 10, in step S17, the controller 12 determines whether the measured knee angle θn measured in step S16 falls within the parameter range for the knee angle θn in the same manner as step S12. Furthermore, the controller 12 also determines whether the measured hip angle θh measured in step S16 falls within the parameter range for the hip angle θh in the same manner as step S12. Then, the controller 12 outputs the bicycle fitting information (i.e., the indicators M11 and M12) on the display screen 48 of the computer system 46 shown in FIG. 12 in the same manner as step S12.

As shown in FIG. 10, if the controller 12 determines that the measured knee angle θn measured in step S16 falls outside the parameter range for the knee angle θn in the same manner as step S12 ("No" in step S18), then the process returns to step S13. In other words, while the indicator M11 on the display screen 48 is displayed in red, the processes from step S13 to S18 are repeated until the indicator M11 is displayed in green or yellow. In this case, the suitable seat position (X2, Y2) of the seat 26 calculated in step S14 will be updated as a temporal bicycle component position while the measured knee angle θn measured in step S11 or step S16 falls outside the parameter range for the knee angle θn. In other words, the controller 12 is further programmed to determine the temporal bicycle component position of the seat 26 (e.g., the bicycle component) based on the rider body parameters in response to measured knee angle θn (e.g., the one of the rider body parameters) falling outside the parameter range of the measured knee angle θn (e.g., the one of the rider body parameters). Then, the bicycle fitting equipment 16 is adjusted based on the temporal bicycle component position in step S17. On the other hand, if the controller 12 determines that the measured knee angle θn measured in step S16 falls within the parameter range for the knee angle θn in the same manner as step S12 ("Yes" in step S18), then the process proceeds to step S21 in FIG. 11. In other words, when the indicator M11 on the display screen 48 is displayed in green or yellow, the adjustment of the seat 26 is completed.

Next, as shown in step S21 in FIG. 11, the controller 12 calculates the position (X3, Y3) of the handlebar 24 (the LED M8) with respect to the position (X0, Y0) of the LED M3 using the measured rider body parameters of the rider body 18 measured in step S16, such as the first to fifth lengths l1 to l5, the first deviation s, the second deviation t, the knee angle θn, the hip angle θh, the armpit angle θ4, and the elbow angle θ5 for example. For example, as shown in FIG. 4, the position (X3, Y3) of the handlebar 24 with respect to the position (X0, Y0) of the LED M3 is calculated based on Equations (26) and (27) below using measured rider body parameters of the rider body 18 measured in step S16 (or S24). Equations (26) and (27) will be described in detail later. In the illustrated embodiment, the position (X0, Y0) of the LED M3 is used as a reference position to calculate the relative position (X3, Y3) of the handlebar 24. Thus, the position (X0, Y0) of the LED M3 can be set as (0, 0). In the illustrated embodiment, the calculated position (X3, Y3) that is calculated for the first time after starting the bicycle fitting process is stored in the memory of the computer system 46 as an initial handlebar position.

Furthermore, the controller 12 determines the suitable handlebar position (X3, Y3) of the handlebar 24 using the target value for the hip angle θh (step S22 in FIG. 11). The target value for the hip angle θh has been determined using the parameter range table 62 based on the hip flexibility level of the hip angle θa (FIG. 2), the bicycle type and the riding type.

Referring now to FIG. 4, determination of the suitable handlebar position (X3, Y3) of the handlebar 24 for the rider by the controller 12 will be described. As shown in FIG. 4, in regards to a knee angle θn2, the relationships expressed by the following Equations are established using the first length l1, the second length l2, and the crank arm length r.

$$X_0'' = X_0$$

$$Y_0'' = Y_0 + 2r$$

$$(X_2 - X_0'')^2 + (Y_2 - Y_0'')^2 = l_2^2 + l_1^2 - 2l_1 l_2 \cos\theta_{n2}$$

$$\therefore \cos\theta_{n2} = -\frac{(X_2 - X_0'')^2 + (Y_2 - Y_0'')^2 - l_2^2 - l_1^2}{2l_1 l_2} = C$$

Here, the knee angle θn2 is defined as an angle at the LED M4 enclosed by the lines from the LED M4 to the LED M5 and the LED M4 to the LED M3 when the crank arm 38 of the crank assembly 28 is vertically oriented at the top dead center. Furthermore, (X0", Y0") indicates the position of the LED M3 when the crank arm 38 of the crank assembly 28 is vertically oriented at the top dead center, while (X2, Y2) indicates the position of the LED M5.

Thus, the knee angle θn2 is expressed according to the following Equation (20).

$$\theta_{n2} = \cos^{-1} C \qquad (20)$$

Furthermore, in regards to an angle γ, the relationships expressed by the following Equations are established.

$$\frac{\sqrt{(X_2 - X_0'')^2 + (Y_2 - Y_0'')^2}}{\sin\theta_{n2}} = \frac{l_2}{\sin\gamma}$$

$$\therefore \sin\gamma = \frac{l_2 \sin\theta_{n2}}{\sqrt{(X_2 - X_0'')^2 + (Y_2 - Y_0'')^2}} = D$$

Here, the angle γ is defined as an angle at the LED M3 enclosed by the lines from the LED M3 to the LED M4 and the LED M3 to the LED M5 when the crank arm 38 of the crank assembly 28 is vertically oriented at the top dead center.

Thus, the angle γ is expressed according to the following Equation (21).

$$\gamma = \sin^{-1} D \qquad (21)$$

In regards to a lower leg angle θ1" and the angle γ, the relationship expressed by the following Equation (22) is established.

$$\frac{Y_2 - Y_0''}{X_2 - X_0''} = \tan(\theta_1^* + \gamma) \qquad (22)$$

$$\therefore \theta_1'' + \gamma = \mathrm{Tan}^{-1}\left(\frac{Y_2 - Y_0^*}{X_2 - X_0^*}\right)$$

Here, the lower leg angle $\theta 1''$ is defined as an angle at the LED M3 enclosed by the horizontal line extending through the LED M3 and the line from the LED M3 to the LED M4 when the crank arm 38 of the crank assembly 28 is vertically oriented at the top dead center.

Based on Equations (21) and (22), the relationship expressed by the following Equation (23) is established.

$$\theta_1'' = \mathrm{Tan}^{-1}\left(\frac{Y_2 - Y_0''}{X_2 - X_0''}\right) - \mathrm{Sin}^{-1} D \qquad (23)$$

Furthermore, in regards to an upper leg angle $\theta 2''$ and a back angle $\theta_{back}$, the relationships expressed by the following Equations (24) and (25) are established.

$$\theta_2'' = 180 - (\theta_{n2} - \theta_1'') \qquad (24)$$

$$\theta_{back} = \theta_h - (180 - \theta_2'') \qquad (25)$$

Here, the upper leg angle $\theta 2''$ is defined as an angle at the LED M4 enclosed by the horizontal line extending through the LED M4 and the line from the LED M4 to the LED M5 when the crank arm 38 of the crank assembly 28 is vertically oriented at the top dead center. Furthermore, the back angle $\theta_{back}$ is defined as an angle at the LED M5 enclosed by the horizontal line extending through the LED M5 and the line from the LED M5 to the LED M6.

Accordingly, the handlebar position (X3, Y3) can be calculated by the following Equations (26) and (27).

$$X_3 = X_2 + l_3 \cos\theta_{back} + l_4 \cos(180 - \theta_{back} - \theta_4) + l_5 \cos(\theta_5 - (180 - |180 - \theta_{back} - \theta_4|)) \qquad (26)$$

$$Y_3 = Y_2 + l_3 \sin\theta_{back} + l_4 \sin(180 - \theta_{back} - \theta_4) + l_5 \sin(\theta_5 - (180 - |180 - \theta_{back} - \theta_4|)) \qquad (27)$$

In the illustrated embodiment, the controller 12 calculates the suitable handlebar position (X3, Y3) based on the above-mentioned Equations (26) and (27). Specifically, the controller 12 calculates the lower leg angle $\theta 1''$ based on Equation (23) using the seat position (X2, Y2), the first length l1, the second length l2, the crank arm length r. In the illustrated embodiment, the controller 12 calculates the lower leg angle $\theta 1''$ based on Equation (23) using the measured values of the first length l1 and the second length l2 that have been measured as explained above, and the preset value of the crank arm length r. Furthermore, the controller 12 calculates the lower leg angle $\theta 1''$ based on Equation (23) using the seat position (X2, Y2) calculated in step S14. Furthermore, the controller 12 calculates the upper leg angle $\theta 2''$ based on Equation (24) using the calculated lower leg angle $\theta 1''$, and the knee angle $\theta n2$ calculated based on Equation (20). Furthermore, the controller 12 calculates the back angle $\theta_{back}$ based on Equation (25) using the calculated upper leg angle $\theta 2''$ and the hip angle $\theta h$. Specifically, the controller 12 calculates the back angle $\theta_{back}$ based on Equation (25) using the preset target value of the hip angle $\theta h$. The preset target value of the hip angle $\theta h$ is determined based on the parameter range table 62 shown in FIGS. 5 to 7 according to the hip flexibility level, the bicycle type and the riding type (i.e., the flexibility level of the rider body 18 and the category information).

Then, the controller 12 further calculates the suitable handlebar position (X3, Y3) based on the above-mentioned Equations (26) and (27) using the position (X2, Y2) of the seat 26 calculated in step S14, the third length l3, the fourth length l4, the fifth length l5, the armpit angle $\theta 4$, the elbow angle $\theta 5$, and the back angle $\theta_k$. In the illustrated embodiment, the controller 12 calculates the handlebar position (X3, Y3) based on the above-mentioned Equations (26) and (27) using the measured values of the third to fifth lengths l3 to l5 that have been measured as explained above, the calculated value of the back angle $\theta_{back}$ that has been calculated as mentioned above, and preset values of the armpit angle $\theta 4$ and the elbow angle $\theta 5$. Specifically, the controller 12 sets the preset parameters for the armpit angle $\theta 4$, the elbow angle $\theta 5$ and the first deviation s using the preset parameter table 64 shown in FIG. 8 based on the bicycle type of the category information inputted by the rider or the operator of the bicycle fitting system 10 to the computer system 46. In the illustrated embodiment, the controller 12 calculates Equations (26) and (27) using the preset values of the armpit angle $\theta 4$ and the elbow angle $\theta 5$. However, alternatively, the controller 12 can calculate Equation (26) and (27) using measured values of the armpit angle $\theta 4$ and the elbow angle $\theta 5$. Furthermore, in the illustrated embodiment, the position (X0, Y0) of the LED M3 is used as a reference position to calculate the suitable handlebar position (X3, Y3) of the handlebar 24. Thus, the position (X0, Y0) of the LED M3 can be set as (0, 0).

Figure 13:
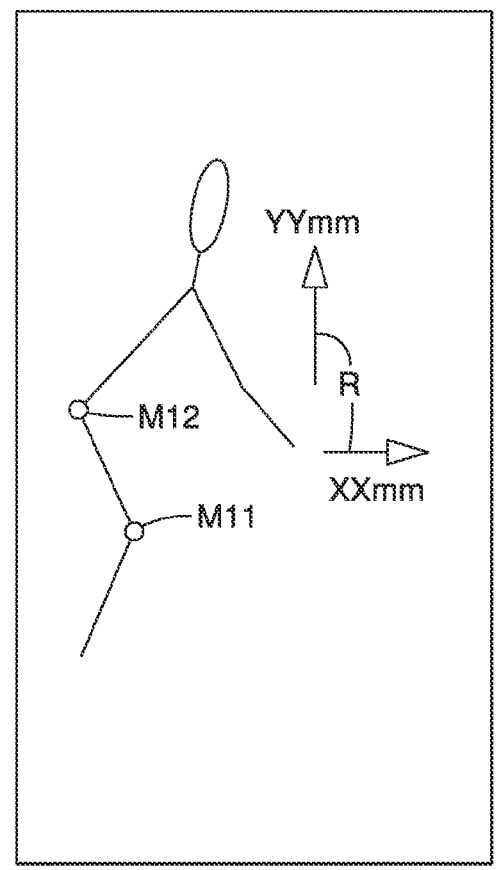
FIG. 13 is a schematic diagram of an display image displayed on the display screen, the display image showing an adjustment direction of the handlebar position and an adjustment amount of the handlebar position.

Next, as shown in FIG. 13, the controller 12 outputs adjustment directions of the handlebar 24 and adjustment amounts of the handlebar 24 on the display screen 48 of the computer system 46 (step S23 in FIG. 11). Specifically, the controller 12 is further programmed to determine the adjustment directions of the handlebar 24 (e.g., the bicycle component) and the adjustment amounts of the handlebar 24 (e.g., the bicycle component) based on the suitable handlebar position (X3, Y3) (e.g., the bicycle component position). Specifically, in the illustrated embodiment, the controller 12 calculates the deviation between the position (X3, Y3) of the handlebar 24 calculated in step S21 and the suitable handlebar position (X3, Y3) of the handlebar 24 calculated in step S22. Specifically, the controller 12 subtract the position (X3, Y3) of the handlebar 24 calculated in step S21 from the suitable handlebar position (X3, Y3) of the handlebar 24 calculated in step S22 to obtain the adjustment directions of the handlebar 24 and the adjustment amounts of the handlebar 24 in the horizontal direction X and in the vertical direction Y. Then, as shown in FIG. 13, the controller 12 displays arrows R indicative of the adjustment directions of the handlebar 24 together with the adjustment amounts of the handlebar 24. In other words, the controller 12 is further programmed to output the adjustment directions and the adjustment amounts on the display screen 48 (e.g., the output apparatus). In the illustrated embodiment, the indicators M11 and M12, the adjustment directions and the adjustment amounts are displayed in the same display image as shown in FIG. 13. However, alternatively, the indicators M11 and M12, the adjustment directions and the adjustment amounts can be displayed in different display images, respectively.

The rider or the operator of the bicycle fitting system 10 adjusts the handlebar 24 with respect to the frame 22 according to the graphic image displayed on the display screen 48. While adjusting the handlebar 24 with respect to the frame 22, the bicycle fitting equipment 16 can output the adjustment data indicative of the actual handlebar adjustment amounts to the controller 12 in the horizontal direction X and in the vertical direction Y as ($\Delta x2$, $\Delta y2$). The controller 12 further outputs the adjustment directions of the handlebar 24 and the adjustment amounts of the handlebar 24 according to the handlebar adjustment amounts (Δx2, Δy2) from the bicycle fitting equipment 16. Specifically, if the handlebar adjustment amounts (Δx2, Δy2) from the bicycle fitting equipment 16 match with the adjustment amounts calculated in step S23, then the arrows R on the display screen 48 disappear to notify that the adjustment of the handlebar 24 with respect to the frame 22 has been completed.

Next, the controller 12 measures the set of the rider body parameters of the rider body 18 while the rider rotates the crank assembly 28 ten times in the same manner as step S11 (step S24 in FIG. 11).

As shown in FIG. 11, in step S25, the controller 12 determines whether the measured knee angle θn measured in step S24 falls within the parameter range for the knee angle θn in the same manner as step S12. Furthermore, the controller 12 also determines whether the measured hip angle θh measured in step S24 falls within the parameter range for the hip angle θh in the same manner as step S12. Then, the controller 12 outputs the bicycle fitting information (i.e., the indicators M11 and M12) on the display screen 48 of the computer system 46 shown in FIG. 13 in the same manner as step S12.

As shown in FIG. 11, if the controller 12 determines that the measured hip angle θh measured in step S24 falls outside the parameter range for the hip angle θh in the same manner as step S12 ("No" in step S26), then the process returns to step S21. In other words, while the indicator M12 on the display screen 48 is displayed in red, the processes from step S21 to S26 are repeated until the indicator M12 is displayed in green or yellow. In this case, the suitable handlebar position (X3, Y3) of the handlebar 24 calculated in step S22 will be updated as a temporal bicycle component position while the measured hip angle θh measured in step S16 or step S24 falls outside the parameter range for the hip angle θh. In other words, the controller 12 is further programmed to determine the temporal bicycle component position of the handlebar 24 (e.g., the bicycle component) based on the rider body parameters in response to measured hip angle θh (e.g., the one of the rider body parameters) falling outside the parameter range of the measured hip angle θh (e.g., the one of the rider body parameters). Then, the bicycle fitting equipment 16 is adjusted based on the temporal bicycle component position in step S25. On the other hand, if the controller 12 determines that the measured hip angle θh measured in step S24 falls within the parameter range for the hip angle θh in the same manner as step S12 ("Yes" in step S26), then the bicycle fitting process is completed. In other words, when the indicator M12 on the display screen 48 is displayed in green or yellow, the adjustment of the handlebar 24 is completed.

Figure 14:
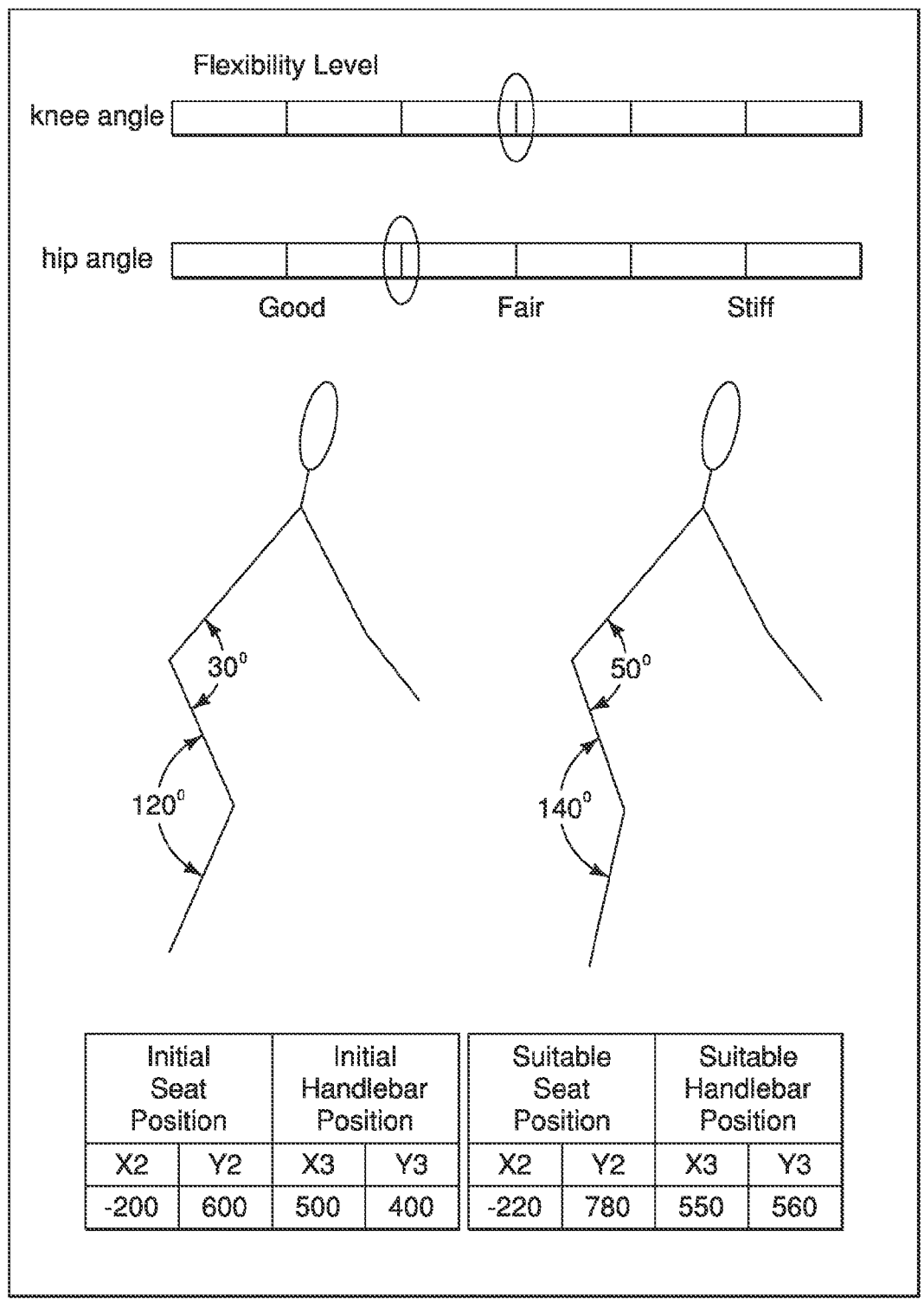
FIG. 14 is a schematic diagram of a display image displayed on the display screen, the display image showing a bicycle fitting result.

After determining the suitable seat position (X2, Y2) and the suitable handlebar position (X3, Y3), the controller 12 output the bicycle fitting information on the display screen 48. In the illustrated embodiment, the controller 12 output the bicycle fitting information as shown in FIG. 14 in response to the rider or the operator of the bicycle fitting system 10 pressing a finish button provided by the bicycle fitting software. However, the controller 12 can automatically output the bicycle fitting information as shown in FIG. 14 in response to the controller 12 determining that the measured hip angle θh measured in step S24 falls within the parameter range for the hip angle θh in step S26. In the illustrated embodiment, as shown in FIG. 14, the controller 12 graphically displays the measured flexibility levels (i.e., the knee flexibility level "knee angle", and the hip flexibility level "hip angle") as the bicycle fitting information.

Furthermore, as shown in FIG. 14, the controller 12 also graphically displays the initial body parameters and the adjusted body parameters as the bicycle fitting information. In particular, the controller 12 outputs a graphic image showing the initial value of the knee angle θn ("120 degree" in FIG. 14) and the initial value of the hip angle θh ("30 degree" in FIG. 14) that are measured in step S11 in FIG. 10. On the other hand, the controller 12 also outputs a graphic image showing the adjusted value of the knee angle θn ("140 degree" in FIG. 14) and the adjusted value of the hip angle θh ("50 degree" in FIG. 14) that are measured in step S24 in FIG. 11 for the last time.

Moreover, as shown in FIG. 14, the controller 12 graphically displays the initial seat position (X2, Y2), the initial handlebar position (X3, Y3), the suitable seat position (X2, Y2), and the suitable handlebar position (X3, Y3) on the orthogonal coordinate system with the axes extending in the horizontal direction X and in the vertical direction Y, respectively, as the bicycle fitting information to reflect the positions to the user's bicycle. The orthogonal coordinate system has the origin at the center axis of the crank axle 42. One parameter Y indicates the vertical position, while the other parameter X indicates the horizontal portion. In other words, the controller 12 is further programmed to output the suitable seat position (X2, Y2) and the suitable handlebar position (X3, Y3) (e.g., the bicycle fitting information) based on the knee angle θn and the hip angle θn (e.g., the rider body parameters), and the parameter ranges of the knee angle θn and the hip angle θn (e.g., the rider body parameters). In the illustrated embodiment, the suitable seat position (X2, Y2) and the suitable handlebar position (X3, Y3) (e.g., the bicycle fitting information) indicates the bicycle component positions of the bicycle component. Furthermore, the controller 12 is further programmed to output the suitable seat position (X2. Y2) and the suitable handlebar position (X3, Y3) (e.g., the bicycle component positions) on the display screen (e.g., the output apparatus). In the illustrated embodiment, the controller 12 is further programmed to acquire the initial seat position (X2, Y2) of the seat 26 and the initial handlebar position (X3. Y3) of the handlebar (e.g., the initial bicycle component positions of the bicycle components). The controller 12 is further programmed to output the suitable seat position (X2, Y2) and the suitable handlebar position (X3, Y3) (e.g., the bicycle component positions), and the initial seat position (X2, Y2) and the initial handlebar position (X3, Y3) (e.g., the initial bicycle component positions). In particular, the controller 12 outputs a graphic image showing the initial seat position (X2, Y2) that is calculated in step S13 in FIG. 10 for the first time, and the initial handlebar position (X3, Y3) that is calculated in step S21 in FIG. 11 for the first time. On the other hand, the controller 12 also outputs a graphic image showing the suitable seat position (X2, Y2) that is calculated in step S14 in FIG. 10 for the last time, and the suitable handlebar position (X3, Y3) that is calculated in step S22 in FIG. 11 for the last time. In the illustrated embodiment, the initial seat position (X2, Y2), the initial handlebar position (X3, Y3), the suitable seat position (X2, Y2), and the suitable handlebar position (X3, Y3) are output as positions relative to the center axis of the crank axle 42. The controller 12 saves the calculation results in a CSV file and the like. In the illustrated embodiment, the controller 12 outputs the bicycle fitting information shown in FIGS. 12 to 14 on the display screen 48. However, alternatively or additionally, the controller 12 can print the bicycle fitting information shown in FIGS. 12 to 14 on a sheet through a printer device.

In understanding the scope of the present invention, the term "coupled" or "coupling", as used herein, encompasses configurations in which an element is directly secured to another element by affixing the element directly to the other element; configurations in which the element is indirectly secured to the other element by affixing the element to the intermediate member(s) which in turn are affixed to the other element; and configurations in which one element is integral with another element, i.e. one element is essentially part of the other element. This definition also applies to words of similar meaning, for example, "joined", "connected", "attached", "mounted", "bonded", "fixed" and their derivatives.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

Also it will be understood that although the terms "first" and "second" may be used herein to describe various components these components should not be limited by these terms. These terms are only used to distinguish one component from another. Thus, for example, a first component discussed above could be termed a second component and vice-a-versa without departing from the teachings of the present invention. Also, the terms "part," "section," "portion," "member" or "element" when used in the singular can have the dual meaning of a single part or a plurality of parts. Finally, terms of degree such as "substantially", "about" and "approximately" as used herein mean an amount of deviation of the modified term such that the end result is not significantly changed.

While only a preferred embodiment has been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired so long as they do not substantially affect their intended function. Components that are shown directly connected or contacting each other can have intermediate structures disposed between them unless specifically stated otherwise. The functions of one element can be performed by two, and vice versa unless specifically stated otherwise. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiment according to the present invention are provided for illustration only, and not for the purpose of limiting the invention as defined by the appended claims and their equivalents.

What is claimed is:

1. A bicycle fitting system comprising:
   a controller programmed to determine whether a current rider position of a rider satisfies a predetermined condition, the predetermined condition being based on a flexibility level of a rider body of the rider, the flexibility level expressing a flexibility of at least one joint of the rider body in terms of a flexibility category selected from at least two different flexibility categories; and
   a motion capturing apparatus electrically connected to the controller, the motion capturing apparatus including at least three markers configured to be attached to a rider body of a rider,
   a sensor configured to detect positions of the at least three markers while the rider is on a bicycle fitting equipment configured to simulate riding a bicycle;
   the controller being programmed to determine the current rider position by measuring at least one rider body parameter of the rider body using the motion capturing apparatus while the rider is on the bicycle fitting equipment, the at least one rider body parameter including at least one angle between three of the markers,
   the controller being programmed to determine whether the predetermined condition is satisfied by determining whether the at least one angle lies within a parameter range selected based on the flexibility level of the rider body, and
   the controller being programmed to calculate bicycle fitting information indicating a bicycle component position of a bicycle component based on the current rider position and the selected parameter range, and output the bicycle fitting information to an output apparatus.

2. The bicycle fitting system according to claim 1, wherein the controller is further programmed to determine the flexibility level using the motion capturing apparatus.

3. The bicycle fitting system according to claim 2, wherein the controller is further programmed to determine the flexibility level by measuring an angle of the at least one joint using the motion capturing apparatus while the rider lies on the rider's back.

4. The bicycle fitting system according to claim 2, wherein the controller is further programmed to determine the flexibility level by comparing an angle of the at least one joint measured using the motion capturing apparatus to a table of data.

5. The bicycle fitting system according to claim 2, wherein the at least one joint includes at least a knee joint or a hip joint of the rider.

6. The bicycle fitting system according to claim 1, wherein the controller is further programmed to
   acquire category information indicative of at least one of a bicycle type and a riding type, and
   set the parameter range of the one of the at least one rider body parameter based on the flexibility level and the category information.

7. The bicycle fitting system according to claim 1, wherein the controller is further programmed to determine a setting position of at least one of a bicycle seat and a bicycle handle as the bicycle component position.

8. The bicycle fitting system according to claim 1, wherein the controller is further programmed to determine a temporal bicycle component position of a bicycle component based on the rider body parameters in response to the one of the rider body parameters falling outside the parameter range of the one of the rider body parameters and,
   the bicycle fitting equipment is adjusted based on the temporal bicycle component position.

9. The bicycle fitting system according to claim 1, wherein the controller is further programmed to output the bicycle component position on the output apparatus.

10. The bicycle fitting system according to claim 9, wherein
   the controller is further programmed to acquire an initial bicycle component position of the bicycle component, and
   the controller is further programmed to output the bicycle component position and the initial bicycle component position.

11. The bicycle fitting system according to claim 1, wherein
the controller is further programmed to determine an adjustment direction of the bicycle component and an adjustment amount of the bicycle component based on the bicycle component position, and
the controller is further programmed to output the adjustment direction and the adjustment amount on the output apparatus.

12. The bicycle fitting sys e according to claim 1, wherein
the controller is further programmed to display an indicator with a first predetermined status in response to the one of the rider body parameters falling within the parameter range of the one of the rider body parameters on a display screen, and
the controller is further programmed to display the indicator with a second predetermined status in response to the one of the rider body parameters falling outside the parameter range of the one of the rider body parameters on the display screen, the second predetermined status being different from the first predetermined status.

13. The bicycle fitting system according to claim 1, wherein
the predetermined condition is a range of angles determined based on the flexibility level, the predetermined condition being satisfied if an angle of the at least one joint is within the range of angles while the rider is on a bicycle fitting equipment.

14. The bicycle fitting system according to claim 1, wherein
the flexibility level is selected manually by a user.

15. The bicycle fitting system according to claim 1, wherein
the flexibility level is inputted to the bicycle fitting system electrically.

* * * * *